US008153125B2

(12) United States Patent
Watkins et al.

(10) Patent No.: US 8,153,125 B2
(45) Date of Patent: *Apr. 10, 2012

(54) CD20 BINDING MOLECULES

(75) Inventors: Jeffry D. Watkins, Encinitas, CA (US); Julian Davies, La Jolla, CA (US); David M. Marquis, Encinitas, CA (US); Barrett W Allan, Encinitas, CA (US); Brian Ondek, San Diego, CA (US)

(73) Assignee: Applied Molecular Evolution, Inc., San Diego, CA (US)

( * ) Notice: Subject to any disclaimer, the term of this patent is extended or adjusted under 35 U.S.C. 154(b) by 696 days.

This patent is subject to a terminal disclaimer.

(21) Appl. No.: 10/553,938

(22) PCT Filed: May 20, 2004

(86) PCT No.: PCT/US2004/015786
§ 371 (c)(1),
(2), (4) Date: Oct. 21, 2005

(87) PCT Pub. No.: WO2004/103404
PCT Pub. Date: Dec. 2, 2004

(65) Prior Publication Data
US 2006/0251652 A1 Nov. 9, 2006

Related U.S. Application Data

(60) Provisional application No. 60/471,958, filed on May 20, 2003.

(51) Int. Cl.
*A61K 39/395* (2006.01)
*C07K 16/28* (2006.01)
*C07K 16/30* (2006.01)

(52) U.S. Cl. ............... 424/133.1; 424/144.1; 424/153.1; 424/173.1; 424/174.1; 530/387.3; 530/388.73; 530/388.8; 530/388.85

(58) Field of Classification Search ........................ None
See application file for complete search history.

(56) References Cited

U.S. PATENT DOCUMENTS

| 6,455,043 B1 | 9/2002 | Grillo-Lopez |
| 2003/0003097 A1 | 1/2003 | Reff et al. |

FOREIGN PATENT DOCUMENTS

| WO | WO 99/54342 | 10/1999 |
| WO | WO 00/42072 | 7/2000 |
| WO | WO 03/011878 | 2/2003 |

OTHER PUBLICATIONS

Business Wire, "Applied Molecular Evolution Advances Optimized Versions of anti-TNF alpha and anti-CD20 Monoclonal Antibody Therapeutic Candidates", Jan. 3, 2003, pp. 1-4, http://findarticles.com/p/articles/mi_m0EIN/is_2003_Jan3/ai_96054855, retrived Jan. 5, 2008.*

AME-133, "Superior Potency Compared to Rituxan® in Ex Vivo Model." Retrieved on Jun. 14, 2004 from website http://www.amevolution.com/Development.
"Auristatin E ADCs, Seattle Genetics," retrieved on Jun. 14, 2004 from website http://www.iddb.com.
Blake, D. et al., "Metal Binding Properties of a Monoclonal Antibody Directed Toward Metal-Chelate Complexes." The Journal of Biological Chemistry, vol. 271, No. 44, pp. 27677-27685, 1996.
Brensing-Kuppers, J. et al., "The Human Immunoglobulin κ Locus on Yeast Artificial Chromosomes (YACs)." Gene, vol. 191, pp. 173-181, 1997.
"(BW) (CA-Genentech/IDEC) (DNA) (IDPH) Genentech and IDEC Announce Humanized Anti-CD20 Antibody Development Collaboration," retrieved on Jun. 14, 2004 from website http://www.businesswire.com.
Cheson, B., "Bexxar Corixa/GlaxoSmithKline." Current Opinion in Investigational Drugs, vol. 3, No. 1, pp. 165-170, 2002.
Chiu, Ya-Wen et al., "Selective Binding of Polychlorinated Biphenyl Congeners by a Monoclonal Antibody: Analysis by Kinetic Exclusion Fluorescence Immunoassay." Anal. Chem, vol. 73, pp. 5477-5484, 2001.
Dall' Acqua et al., "Increasing the Affinity of a Human IgG1 for the Neonatal Fc Receptor: Biological Consequences." The Journal of Immunology, vol. 169, pp. 5171-5180, 2002.
Edwards, J. and Cambridge, G., "Sustained Improvement in Rheumatoid Arthritis Following a Protocol Designed to Deplete B Lymphocytes." Rheumatology, vol. 40, No. 2, pp. 205-211, 2001.
"GENMAB Announces Humax-CD20 Program," retrieved on Jun. 14, 2004 from website http://www.genmab.com.
"GENMAB: Selected Genmab Literature," retrieved on Jun. 14, 2004 from website http://www.genmab.com.
"GENENTECH and IDEC Announce Humanized Anti-CD20 Antibody Development Collaboration," retrieved on Jun. 23, 2003 from website http://biz.yahoo.com.
Ghetie, V. et al., "Increasing the Serum Persistence of an IgG Fragment by Random Mutagenesis." Nature Biotechnology, vol. 15, pp. 637-640, 1997.
Hongo, J. et al., "Characterization of Novel Neutralizing Monoclonal Antibodies Specific to Human Neurturin." Hybridoma, vol. 19, No. 4, pp. 303-315, 2000.
"HUMAX-CD20," retrieved on Jun. 14, 2004 from website http://www.iddb.com.
Kawasaki, K. et al., "Evolutionary Dynamics of the Human Immunoglobulin κ Locus and the Germline Repertoire of the Vκ Genes." Eur. J. Immunol., vol. 31, pp. 1017-1028, 2001.
Kawasaki, K. et al., "One-Megabase Sequence Analysis of the Human Immunoglobulin λ Gene Locus." Genome Research, vol. 7, pp. 250-261, 1997.

(Continued)

*Primary Examiner* — Ronald Schwadron
(74) *Attorney, Agent, or Firm* — Robert L. Sharp; Paula K. Davis

(57) ABSTRACT

The present invention relates to CD20 binding molecules and nucleic acid sequences encoding CD20 binding molecules. In particular, the present invention relates to CD20 binding molecules with a high binding affinity, and a low dissociation rate, with regard to human CD20. Preferably, the CD20 binding molecules of the present invention comprise light and/or heavy chain variable regions with fully human frameworks (e.g. human germline frameworks).

11 Claims, 13 Drawing Sheets

OTHER PUBLICATIONS

Khosraviani, M. et al., "Binding Properties of a Monoclonal Antibody Directed Toward Lead-Chelate Complexes." Bioconjugate Chem. vol. 11, pp. 267-277, 2000.

Kim, Jin-Kyoo et al., "Mapping the Site on Human IgG for Binding of the MHC Class 1-Related Receptor, FcRn." Eur. J. Immunol., vol. 29, pp. 2819-2825, 1999.

"Ibritumomab Tiuxetan," retrieved on Jun. 14, 2004 from website http://www.iddb.com.

Illidge, T. and Bayne, M., "Antibody Therapy of Lymphoma." Expert Opin. Pharmacother., vol. 2, No. 6, pp. 953-961, 2001.

Medesan, C. et al., "Comparative Studies of Rat IgG to Further Delineate the Fc: FcRn Interaction Site." Eur. J. Immunol., vol. 28, pp. 2092-2100, 1998.

Powers, D. et al., "Expression of Single-Chain Fv-Fc Fusions in *Pichia pastoris*." Journal of Immunological Methods, vol. 251, pp. 123-135, 2001.

"R-1594," retrieved on Jun. 14, 2004 from website http://www.iddb.com.

"Rituximab," retrieved on Jun. 14, 2004 from website http://www.iddb.com.

Schable and Zachau, "The Variable Genes of the Human Immunoglobulin χ Locus." Biol. Chem. Hoppe-Seyler, vol. 374, pp. 1001-1022, 1993.

Seldin, D., "Techniques for Using Bexxar for the Treatment of Non-Hodgkin's Lymphoma." Journal of Nuclear Medicine Technology, vol. 30, No. 3, pp. 109-114, 2002.

Shields, R. et al., "High Resolution Mapping of the Binding Site on Human IgG1 for FcγRI, FcγRII, FcγRIII, and FcRn and Design of IgG1 Variants with Improved Binding to the FcγR." The Journal of Biological Chemistry, vol. 276, No. 9, pp. 6591-6604, 2001.

Stein, R. et al., "Characterization of a New Humanized Anti-CD20 Monoclonal Antibody, IMMU-106, and Its Use in Combination with the Humanized Anti-CD22 Antibody, Epratuzumab, for the Therapy of Non-Hodgkin's Lymphoma." Clinical Cancer Research, vol. 10, pp. 2868-2878, 2004.

"TOSITUMOMAB," retrieved on Jun. 14, 2004 from website http://www.iddb.com.

Umana, P. et al., "Engineered Glycoforms of an Antineuro-blastoma IgG1 with Optimized Antibody-dependent Cellular Cytotoxic Activity." Nature Biotechnology, vol. 17, pp. 176-180, 1999.

Vasserot, A. et al., "Optimization of Protein Therapeutics by Directed Evolution." Drug Discovery Today, vol. 8, No. 3, pp. 118-126, 2003.

Wu, H., "Humanization of a Murine Monoclonal Antibody by Simultaneous Optimization of Framework and CDR Residues." J. Mol. Biol., vol. 294, pp. 151-162, 1999.

* cited by examiner

| | |
|---|---|
| ▭ | domains |
| ∿∿ | inter-domain sections |
| — | disulphide bonds |
| V | variable |
| C | constant |
| L | light chain |
| H | heavy chain |

SEQ ID NO:59 - AME 33 light chain variable region amino acid sequence

EIVLTQSPGTLSLSPGERATLSCRASSSVPYIHWYQQKPGQAPRLLIYATSALASGI
PDRFSGSGSGTDFTLTISRLEPEDFAVYYCQQWLSNPPTFGQGTKLEIK

B.

SEQ ID NO:60 - AME 33 light chain variable region nucleic acid sequence

GAAATTGTGTTGACGCAGTCTCCAGGCACCCTGTCTTTGTCTCCAGGGGAAAG
AGCCACCCTCTCCTGCAGGGCCAGCTCAAGTGTACCGTACATCCACTGGTAC
CAGCAGAAACCTGGCCAGGCTCCCAGGCTCCTCATCTATGCCACATCCGCTCT
GGCTTCTGGCATCCCAGACAGGTTCAGTGGCAGTGGGTCTGGGACAGACTTC
ACTCTCACCATCAGCAGACTGGAGCCTGAAGATTTTGCAGTGTATTACTGTCA
GCAGTGGCTGAGTAACCCACCCACTTTTGGCCAGGGGACCAAGCTGGAGATC
AAA

SEQ ID NO:61 - AME 33 heavy chain variable region amino acid sequence

EVQLVQSGAEVKKPGESLKISCKGSGRTFTSYNMHWVRQMPGKGLEWMGAIYP
LTGDTSYNQKSKLQVTISADKSISTAYLQWSSLKASDTAMYYCARSTYVGGDW
QFDVWGKGTTVTVSS

B.

SEQ ID NO:62 - AME 33 heavy chain variable region nucleic acid sequence

GAGGTGCAGCTGGTGCAGTCTGGAGCAGAGGTGAAAAAGCCCGGGGAGTCT
CTGAAGATCTCCTGTAAGGGTTCTGGCCGTACATTTACCAGTTACAATATGCA
CTGGGTGCGCCAGATGCCCGGGAAAGGCCTGGAGTGGATGGGGGCTATTTAT
CCCTTGACGGGTGATACTTCCTACAATCAGAAGTCGAAACTCCAGGTCACCA
TCTCAGCCGACAAGTCCATCAGCACCGCCTACCTGCAGTGGAGCAGCCTGAA
GGCCTCGGACACCGCCATGTATTACTGTGCGAGATCGACTTACGTGGGCGGT
GACTGGCAGTTCGATGTCTGGGGCAAGGGGACCACGGTCACCGTCTCCTCA

SEQ ID NO:63 - AME 5 light chain variable region amino acid sequence

DIQMTQSPSSLSASVGDRVTITCRASSSVHYIHWYQQKPGKVPKLLIYATSGLAS
GVPSRFSGSGSGTDFTLTISSLQPEDVATYYCQTWTFNPPTFGGGTKVEIK

B.

SEQ ID NO:64 - AME 5 light chain variable region nucleic acid sequence

GACATCCAGATGACCCAGTCTCCATCCTCCCTGTCTGCATCTGTAGGA
GACAGAGTCACCATCACTTGCAGGGCCAGCTCAAGTGTACATTACATC
CACTGGTACCAGCAGAAACCAGGGAAAGTTCCTAAGCTCTTGATCTAT
GCCACATCCGGCCTGGCTTCTGGGGTCCCATCTCGGTTCAGTGGCAGT
GGATCTGGGACAGATTTCACTCTCACCATCAGCAGCCTGCAGCCTGAA
GATGTTGCCACTTATTACTGCCAGACTTGGACTTTTAACCCTCCCACG
TTCGGCGGAGGGACCAAGGTGGAGATCAAA

SEQ ID NO:65 - AME 5 heavy chain variable region amino acid sequence

QVQLVQSGAEVKKPGASVKVSCKASGYTFTSYNMHWVRQAPGQGLEWMGAIY
PGNGDTSYNQKFKWRVTMTRDTSTSTVYMELSSLRSEDTAVYYCARSTYYGGD
WQFDEWGKGTTVTVSS

B.

SEQ ID NO:66 - AME 5 heavy chain variable region nucleic acid sequence

CAGGTGCAGCTGGTGCAGTCTGGTGCTGAAGTGAAGAAGCCTGGGGCC
TCAGTGAAGGTGTCCTGCAAGGCATCTGGATACACCTTCACCAGCTAC
AATATGCACTGGGTGCGACAGGCCCCTGGACAAGGGCTTGAGTGGATG
GGAGCCATCTATCCTGGAAATGGTGATACAAGCTACAATCAGAAGTTT
AAATGGAGAGTCACCATGACCAGGGACACGTCCACGAGCACAGTCTAC
ATGGAGCTGAGCAGCCTGAGATCTGAGGACACGGCCGTGTATTACTGT
GCGAGATCGACTTATTACGGCGGTGACTGGCAGTTCGACGAGTGGGGC
AAAGGGACCACGGTCACCGTCTCCTCA

SEQ ID NO:67 - AME 33 complete light chain amino acid sequence

EIVLTQSPGTLSLSPGERATLSCRASSSVPYIHWYQQKPGQAPRLLIYATSALASGIPDR
FSGSGSGTDFTLTISRLEPEDFAVYYCQQWLSNPPTFGQGTKLEIK<u>RTVAAPSVFIFPPS
DEQLKSGTASVVCLLNNFYPREAKVQWKVDNALQSGNSQESVTEQDSKDSTYSLSST
LTLSKADYEKHKVYACEVTHQGLSSPVTKSFNRGEC</u>

- Constant Region is underlined

B.

SEQ ID NO:68 - AME 33 complete light chain nucleic acid sequence

GAAATTGTGTTGACGCAGTCTCCAGGCACCCTGTCTTTGTCTCCAGGGGAAAGAG
CCACCCTCTCCTGCAGGGCCAGCTCAAGTGTACCGTACATCCACTGGTACCAGCA
GAAACCTGGCCAGGCTCCCAGGCTCCTCATCTATGCCACATCCGCTCTGGCTTCTG
GCATCCCAGACAGGTTCAGTGGCAGTGGGTCTGGGACAGACTTCACTCTCACCAT
CAGCAGACTGGAGCCTGAAGATTTTGCAGTGTATTACTGTCAGCAGTGGCTGAGT
AACCCACCCACTTTTGGCCAGGGGACCAAGCTGGAGATCAAACGAACTGTGGCTG
CACCATCTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACAGTGGA
AGGTGGATAACGCCCTCCAATCGGGTAACTCCCAGGAGAGTGTCACAGAGCAGGA
CAGCAAGGACAGCACCTACAGCCTCAGCAGCACCCTGACGCTGAGCAAAGCAGA
CTACGAGAAACACAAAGTCTACGCCTGCGAAGTCACCCATCAGGGCCTGAGCTCG
CCCGTCACAAAGAGCTTCAACAGGGGAGAGTGTTAG

FIGURE 7

A. SEQ ID NO:69 - AME 33 complete heavy chain amino acid sequence

EVQLVQSGAEVKKPGESLKISCKGSGRTFTSYNMHWVRQMPGKGLEWMGAIYPLTG
DTSYNQKSKLQVTISADKSISTAYLQWSSLKASDTAMYYCARSTYVGGDWQFDVWG
KGTTVTVSS<u>ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISKA
KGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK</u>

- Constant Region is underlined; the "D" at position 280 and "K" at position 290 are in bold

B. SEQ ID NO:70 - AME 33 complete heavy chain nucleic acid sequence

GAGGTGCAGCTGGTGCAGTCTGGAGCAGAGGTGAAAAAGCCCGGGGAGTCTCTG
AAGATCTCCTGTAAGGGTTCTGGCCGTACATTTACCAGTTACAATATGCACTGGGT
GCGCCAGATGCCCGGGAAAGGCCTGGAGTGGATGGGGGCTATTTATCCCTTGACG
GGTGATACTTCCTACAATCAGAAGTCGAAACTCCAGGTCACCATCTCAGCCGACA
AGTCCATCAGCACCGCCTACCTGCAGTGGAGCAGCCTGAAGGCCTCGGACACCGC
CATGTATTACTGTGCGAGATCGACTTACGTGGGCGGTGACTGGCAGTTCGATGTCT
GGGGCAAGGGGACCACGGTCACCGTCTCCTCAGCCTCCACCAAGGGCCCATCGGT
CTTCCCCCTGGCACCCTCCTCCAAGAGCACCTCTGGGGGCACAGCGGCCCTGGGCT
GCCTGGTCAAGGACTACTTCCCCGAACCGGTGACGGTGTCGTGGAACTCAGGCGC
CCTGACCAGCGGCGTGCACACCTTCCCGGCTGTCCTACAGTCCTCAGGACTCTACT
CCCTCAGCAGCGTGGTGACCGTGCCCTCCAGCAGCTTGGGCACCCAGACCTACAT
CTGCAACGTGAATCACAAGCCCAGCAACACCAAGGTGGACAAGAAGGTTGAGCC
CAAATCTTGTGACAAAACTCACACATGCCCACCGTGCCCAGCACCTGAACTCCTG
GGGGGACCGTCAGTCTTCCTCTTCCCCCCAAAACCCAAGGACACCCTCATGATCTC
CCGGACCCCTGAGGTCACATGCGTGGTGGTGGACGTGAGCCACGAAGACCCTGAG
GTCAAGTTCAACTGGTACGTG<u>GAC</u>GGCGTGGAGGTGCATAATGCCAAGACAAAG
CCGCGGGAGGAGCAGTACAACAGCACGTACCGTGTGGTCAGCGTCCTCACCGTCC
TGCACCAGGACTGGCTGAATGGCAAGGAGTACAAGTGCAAGGTCTCCAACAAAG
CCCTCCCAGCCCCCATCGAGAAAACCATCTCCAAAGCCAAAGGGCAGCCCCGAGA
ACCACAGGTGTACACCCTGCCCCCATCCCGGGACGAGCTGACCAAGAACCAGGTC
AGCCTGACCTGCCTGGTCAAAGGCTTCTATCCCAGCGACATCGCCGTGGAGTGGG
AGAGCAATGGGCAGCCGGAGAACAACTACAAGACCACGCCTCCCGTGCTGGACTC
CGACGGCTCCTTCTTCCTCTATAGCAAGCTCACCGTGGACAAGAGCAGGTGGCAG
CAGGGGAACGTCTTCTCATGCTCCGTGATGCATGAGGCTCTGCACAACCACTACA
CGCAGAAGAGCCTCTCCCTGTCTCCGGGTAAATGA

FIGURE 8
A.
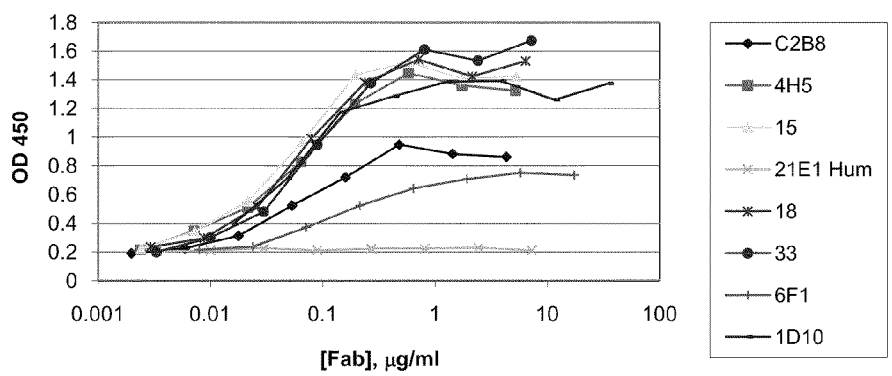
B.
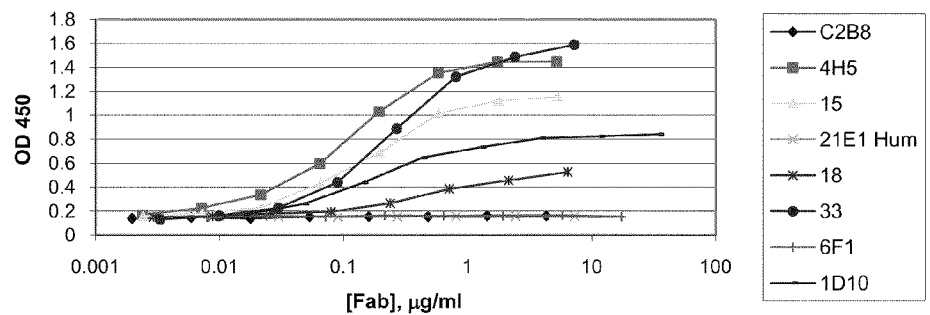
C.
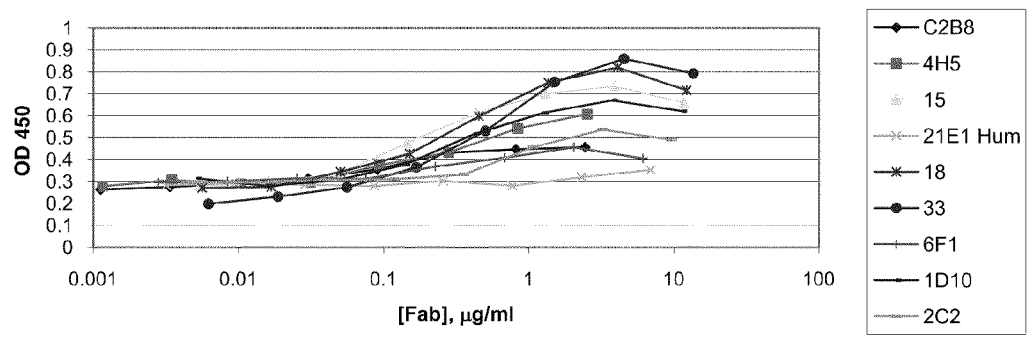

FIGURE 9
A.
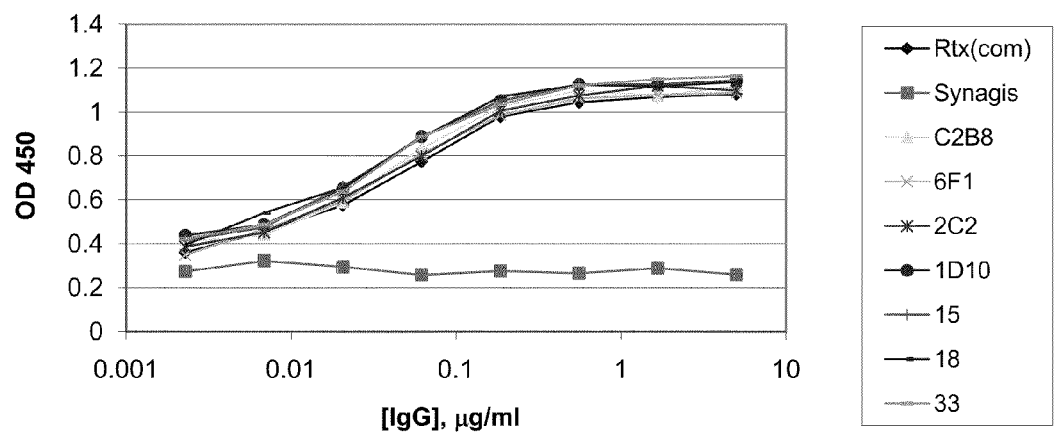
B.
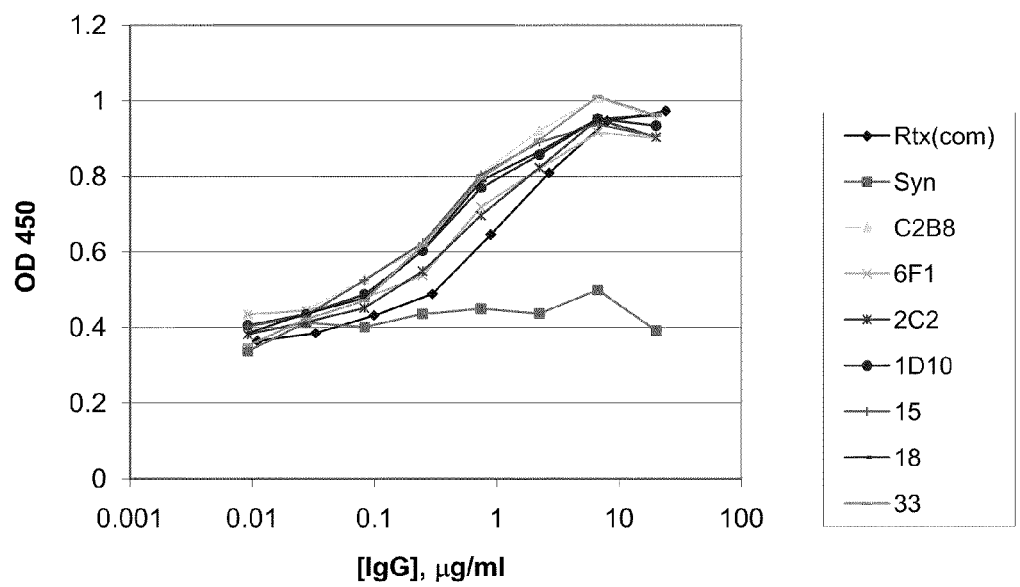

FIGURE 10
A.
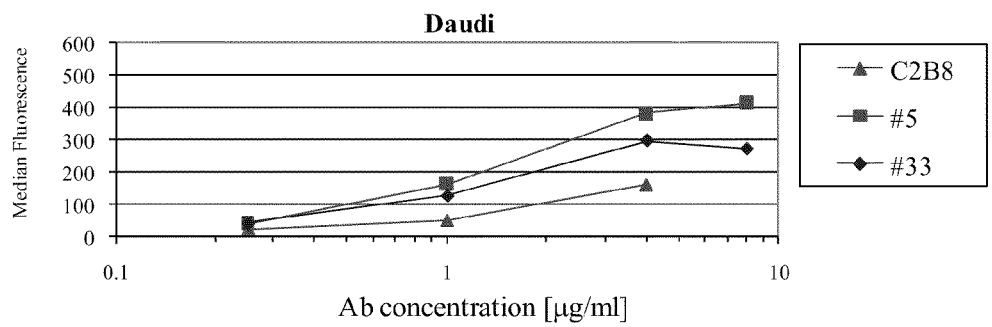
B.
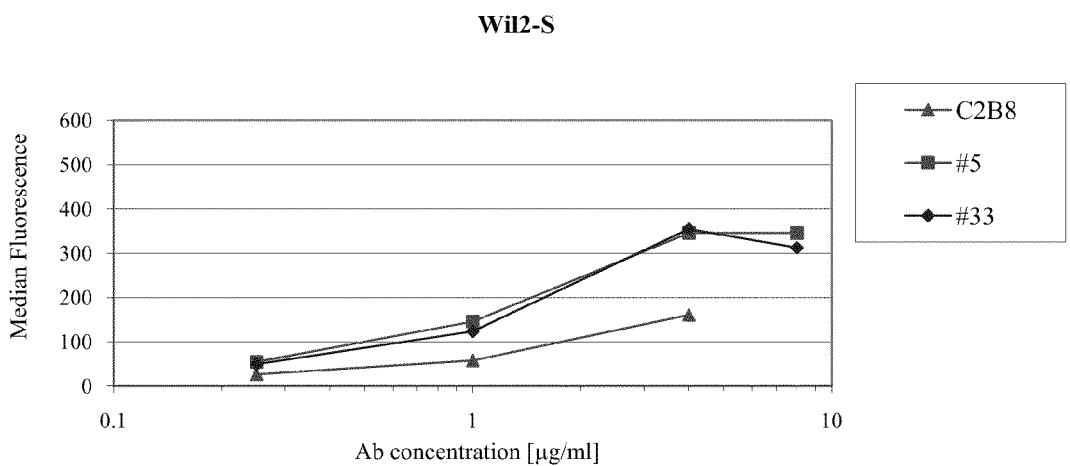
C.
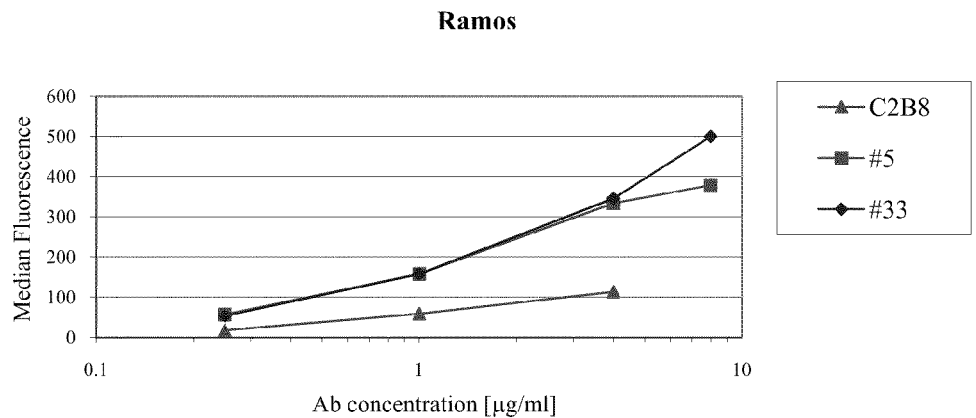

CD20 BINDING MOLECULES

The present Application is a 35 U.S.C. §371 U.S. national-phase application of International Application No. PCT/US2004/015786, international filing date of 20 May 2004, which claims priority to U.S. application Ser. No. 10/849,615, filed May 20, 2004, now abandoned, and U.S. Provisional Application Ser. No. 60/471,958 filed May 20, 2003.

FIELD OF THE INVENTION

The present invention relates to CD20 binding molecules and nucleic acid sequences encoding CD20 binding molecules. In particular, the present invention relates to CD20 binding molecules with a high binding affinity, and a low dissociation rate, with regard to human CD20. Preferably, the CD20 binding molecules of the present invention comprise light and/or heavy chain variable regions with fully human frameworks (e.g. human germline frameworks).

BACKGROUND OF THE INVENTION

The use of antibodies to the CD20 antigen as diagnostic and/or therapeutic agents for diseases such as B-cell lymphoma has previously been reported. CD20 is a useful marker or target for B-cell lymphomas as this antigen is expressed at very high densities on the surface of malignant B-cells, i.e., B-cells wherein unabated proliferation can lead to B-cell lymphomas.

CD20 (also known as Bp35) is a B-lymphocyte-restricted differentiation antigen that is expressed during early pre-B-cell development and remains until plasma cell differentiation. It is believed by some that the CD20 molecule may regulate a step in the B-cell activation process which is required for cell cycle initiation and differentiation. Moreover, as noted, CD20 is usually expressed at very high levels on neoplastic ("tumor") B-cells. The CD20 antigen is appealing for targeted therapy, because it does not shed, modulate, or internalize.

Previous reported therapies involving anti-CD20 antibodies have involved the administration of a therapeutic anti-CD20 antibody either alone or in conjunction with a second radiolabeled anti-CD20 antibody, or a chemotherapeutic agent. The Food and Drug Administration has approved the therapeutic use of one such anti-CD20 antibody, RITUXAN for use in relapsed and previously treated low-grade non-Hodgkin's lymphoma (NHL). However, while the use of RITUXAN has generally been reported as effective for treating B-cell lymphomas, the treated patients are often subject to disease relapse.

More recently, RITUXAN was tested for safety, tolerability and preliminary clinical efficacy for the treatment of 18 patients with Systemic Lupus Erythematosus (SLE) (which are non immunosuppressed patients). Part of the results of this study were presented in October of 2002 at the American College of Rheumatology (ACR) 66th Annual Scientific Meeting. Of the 18 patients treated, six patients received one infusion of RITUXAN at 100 mg/m$^2$ (low dose), six patients received one infusion of RITUXAN at 375 mg/m$^2$ (medium dose), and six patients received four weekly infusions of RITUXAN at 375 mg/m$^2$ (high dose). Three of the 12 patients that received the low or medium dose (25%) developed elevated human anti-chimera (HACA) titers at two months, while the high dose patients are still being evaluated.

Accordingly, what is needed, are CD20 binding molecules that have a high binding affinity and low dissociation constant such that treated B-cell lymphoma patients do not relapse, and CD20 binding molecules that do not cause, or have a reduced potential to cause, a HACA reaction when administered to patients who are not immunosuppressed.

SUMMARY OF THE INVENTION

The present invention provides CD20 binding molecules and nucleic acid sequences encoding CD20 binding molecules. In particular, the present invention provides CD20 binding molecules with a high binding affinity, and a low dissociation rate, with regard to human CD20. Preferably, the CD20 binding molecules of the present invention comprise light and/or heavy chain variable regions with fully human frameworks (e.g. human germline frameworks).

In some embodiments, the present invention provides compositions comprising a CD20 binding molecule, wherein the CD20 binding molecule comprises: a) a light chain variable region, or a portion of a light chain variable region, wherein the light chain variable region (or the portion) comprises; i) a CDRL1 amino acid sequence selected from the group consisting of SEQ ID NO:1, SEQ ID NO:3, and SEQ ID NO:5; ii) a CDRL2 amino acid sequence selected from the group consisting of SEQ ID NO:7, SEQ ID NO:9, SEQ ID NO:11, and SEQ ID NO:13; iii) a CDRL3 amino acid sequence selected from the group consisting of SEQ ID NO:17, SEQ ID NO:19, and SEQ ID NO:21; and b) a heavy chain variable region, or a portion of a heavy chain variable region, wherein the heavy chain variable region (or the portion) comprises; i) a CDRH1 amino acid sequence selected from the group consisting of SEQ ID NO:23 and SEQ ID NO:25; ii) a CDRH2 amino acid sequence selected from the group consisting of SEQ ID NO:27, SEQ ID NO:29, SEQ ID NO:31, SEQ ID NO:33, SEQ ID NO:35, SEQ ID NO:37, and SEQ ID NO:39; and iii) a CDRH3 amino acid sequence selected from the group consisting of SEQ ID NO:43, SEQ ID NO:45, SEQ ID NO:47, SEQ ID NO:49, SEQ ID NO:51, SEQ ID NO:53, SEQ ID NO:55, and SEQ ID NO:57.

In other embodiments, the present invention provides compositions comprising a light chain variable region (or a portion thereof), or a nucleic acid sequence (or a portion thereof) encoding a light chain variable region, wherein the light chain variable region (or the portion thereof) comprises: a) a CDRL1 amino acid sequence selected from the group consisting of SEQ ID NO:1, SEQ ID NO:3, and SEQ ID NO:5; b) a CDRL2 amino acid sequence selected from the group consisting of SEQ ID NO:7, SEQ ID NO:9, SEQ ID NO:11, and SEQ ID NO:13; and c) a CDRL3 amino acid sequence selected from the group consisting of SEQ ID NO:17, SEQ ID NO:19, and SEQ ID NO:21.

In certain embodiments, the present invention provides compositions comprising a heavy chain variable region (or portion thereof), or a nucleic acid sequence (or portion thereof) encoding a heavy chain variable region, wherein the heavy chain variable region (or portion thereof) comprises: a) a CDRH1 amino acid sequence selected from the group consisting of SEQ ID NO:23 and SEQ ID NO:25; b) a CDRH2 amino acid sequence selected from the group consisting of SEQ ID NO:27, SEQ ID NO:29, SEQ ID NO:31, SEQ ID NO:33, SEQ ID NO:35, SEQ ID NO:37, and SEQ ID NO:39; and c) a CDR-H3 amino acid sequence selected from the group consisting of SEQ ID NO:43, SEQ ID NO:45, SEQ ID NO:47, SEQ ID NO:49, SEQ ID NO:51, SEQ ID NO:53, SEQ ID NO:55, and SEQ ID NO:57.

In additional embodiments, the present invention provides compositions comprising: a) a light chain variable region, or a first nucleic acid sequence encoding a light chain variable region, wherein the light chain variable region comprises a CDRL3 amino acid sequence selected from the group consisting of SEQ ID NO:17, SEQ ID NO:19, and SEQ ID NO:21; and b) a heavy chain variable region, or a second nucleic acid sequence encoding a heavy chain variable region, wherein the heavy chain variable region comprises a CDRH3 amino acid sequence selected from the group consisting of SEQ ID NO:43, SEQ ID NO:45, SEQ ID NO:47, SEQ ID NO:49, SEQ ID NO:51, SEQ ID NO:53, SEQ ID NO:55, and SEQ ID NO:57.

In some embodiments, the present invention provides compositions comprising a nucleic acid molecule encoding a light chain variable region of a CD20 binding molecule, wherein the nucleic acid molecule comprises; a) a CDRL1 nucleic acid sequence selected from the group consisting of SEQ ID NO:2, SEQ ID NO:4, and SEQ ID NO:6; b) a CDRL2 nucleic acid sequence selected from the group consisting of SEQ ID NO:8, SEQ ID NO:10, SEQ ID NO:12, and SEQ ID NO:14; and c) a CDRL3 nucleic acid sequence selected from the group consisting of SEQ ID NO:18, SEQ ID NO:20, and SEQ ID NO:22. In other embodiments, the present invention provides compositions comprising a nucleic acid molecule encoding a heavy chain variable region of a CD20 binding molecule, wherein the nucleic acid molecule comprises; a) a CDRH1 nucleic acid sequence selected from the group consisting of SEQ ID NO:24 and SEQ ID NO:26; b) a CDRH2 nucleic acid sequence selected from the group consisting of SEQ ID NO:28, SEQ ID NO:30, SEQ ID NO:32, SEQ ID NO:34, SEQ ID NO:36, SEQ ID NO:38, and SEQ ID NO:40; and c) a CDRH3 nucleic acid sequence selected from the group consisting of SEQ ID NO:44, SEQ ID NO:46, SEQ ID NO:48, SEQ ID NO:50, SEQ ID NO:52, SEQ ID NO:54, SEQ ID NO:56, and SEQ ID NO:58.

In particular embodiments, the present invention provides compositions comprising a CD20 binding molecule, wherein the CD20 binding molecule comprises a) a CDRL1 amino acid sequence comprising SEQ ID NO:5; b) a CDRL2 amino acid sequence comprising SEQ ID NO:13; c) a CDRL3 amino acid sequence comprising SEQ ID NO:19; d) a CDRH1 amino acid sequence comprising SEQ ID NO:25; e) a CDRH2 amino acid sequence comprising SEQ ID NO:39; and f) a CDRH3 amino acid sequence comprising SEQ ID NO:57. In other embodiments, the present invention provides compositions comprising a nucleic acid molecule encoding a light chain variable region of a CD20 binding molecule, wherein the nucleic acid molecule comprises a) a CDRL1 nucleic acid sequence comprising SEQ ID NO:6; b) a CDRL2 nucleic acid sequence comprising SEQ ID NO:14; and c) a CDRL3 nucleic acid sequence comprising SEQ ID NO:20.

In further embodiments, the present invention provides compositions comprising a nucleic acid molecule encoding a heavy chain variable region of a CD20 binding molecule, wherein the nucleic acid molecule comprises a) a CDRH1 nucleic acid sequence comprising SEQ ID NO:26; b) a CDRH2 nucleic acid sequence comprising SEQ ID NO:40; and c) a CDRH3 nucleic acid sequence comprising SEQ ID NO:58. In other embodiments, the present invention provides compositions comprising: a) a first nucleic acid sequence encoding a light chain variable region, wherein the first nucleic acid sequence comprises a CDRL3 nucleic acid sequence selected from the group consisting of SEQ ID NO:18, SEQ ID NO:20, and SEQ ID NO:22; and b) a second nucleic acid sequence encoding a heavy chain variable region, wherein the second nucleic acid sequence comprises a CDRH3 nucleic acid sequence selected from the group consisting of SEQ ID NO:44, SEQ ID NO:46, SEQ ID NO:48, SEQ ID NO:50, SEQ ID NO:52, SEQ ID NO:54, SEQ ID NO:56, and SEQ ID NO:58.

In some embodiments, the present invention provides compositions comprising: a) a first nucleic acid sequence encoding a light chain variable region, wherein the light chain variable region comprises; i) a CDRL1 amino acid sequence selected from the group consisting of SEQ ID NO:1, SEQ ID NO:3, and SEQ ID NO:5; ii) a CDRL2 amino acid sequence selected from the group consisting of SEQ ID NO:7, SEQ ID NO:9, SEQ ID NO:11, and SEQ ID NO:13; and iii) a CDRL3 amino acid sequence selected from the group consisting of SEQ ID NO:17, SEQ ID NO:19, and SEQ ID NO:21; and b) a second nucleic acid sequence encoding a heavy chain variable region, wherein the heavy chain variable region comprises; i) a CDRH1 amino acid sequence selected from the group consisting of SEQ ID NO:23 and SEQ ID NO:25; ii) a CDRH2 amino acid sequence selected from the group consisting of SEQ ID NO:27, SEQ ID NO:29, SEQ ID NO:31, SEQ ID NO:33, SEQ ID NO:35, SEQ ID NO:37, and SEQ ID NO:39; and iii) a CDRH3 amino acid sequence selected from the group consisting of SEQ ID NO:43, SEQ ID NO:45, SEQ ID NO:47, SEQ ID NO:49, SEQ ID NO:51, SEQ ID NO:53, SEQ ID NO:55, and SEQ ID NO:57.

In some embodiments, the present invention provides a peptide comprising at least two (or at least three or four) CDRs selected from the group consisting of SEQ ID NO:1, SEQ ID NO:3, SEQ ID NO:5; SEQ ID NO:7, SEQ ID NO:9, SEQ ID NO:11, SEQ ID NO:13; SEQ ID NO:17, SEQ ID NO:19, and SEQ ID NO:21. In other embodiments, the present invention provides a peptide comprising at least two (or at least three or four) CDRs selected from the group consisting of SEQ ID NO:23, SEQ ID NO:25; SEQ ID NO:27, SEQ ID NO:29, SEQ ID NO:31, SEQ ID NO:33, SEQ ID NO:35, SEQ ID NO:37, SEQ ID NO:39; of SEQ ID NO:43, SEQ ID NO:45, SEQ ID NO:47, SEQ ID NO:49, SEQ ID NO:51, SEQ ID NO:53, SEQ ID NO:55, and SEQ ID NO:57.

In certain embodiments, the present invention provides a composition comprising a light chain variable region and a heavy chain variable region, wherein the light chain variable region comprises an amino acid sequence selected from the group consisting of SEQ ID NO:1, SEQ ID NO:3, SEQ ID NO:5; SEQ ID NO:7, SEQ ID NO:9, SEQ ID NO:11, SEQ ID NO:13; SEQ ID NO:17, SEQ ID NO:19, and SEQ ID NO:21; and wherein the heavy chain variable region comprises an amino acid sequence selected from SEQ ID NO:23, SEQ ID NO:25; SEQ ID NO:27, SEQ ID NO:29, SEQ ID NO:31, SEQ ID NO:33, SEQ ID NO:35, SEQ ID NO:37, SEQ ID NO:39; of SEQ ID NO:43, SEQ ID NO:45, SEQ ID NO:47, SEQ ID NO:49, SEQ ID NO:51, SEQ ID NO:53, SEQ ID NO:55, and SEQ ID NO:57.

In certain embodiments, the light chain variable region comprises a portion of a framework (e.g. containing 2 or 3 subregions, such as FR2 and FR3). In some embodiments, the light chain variable region comprises a fully human framework. In other embodiments, the light chain variable region comprise a human germline framework. In particular embodiments, the light chain variable region comprises an amino acid sequence selected from SEQ ID NO:59, and 63. In certain embodiments, the heavy chain variable region comprises a portion of a framework (e.g. containing 2 or 3 subregions, such as FR2 and FR3). In certain embodiments, the heavy chain variable region comprises a fully human framework. In other embodiments, the heavy chain variable region comprises a human germline framework. In additional embodiments, the heavy chain variable region comprises an amino acid sequence selected from 61, and 65.

In some embodiments, the CD20 binding molecule comprises an antibody or antibody fragment (e.g., Fv, Fab, etc.).

In particular embodiments, the CD20 binding molecule comprises the AME 33 Fv or Fab. In other embodiments, the CD20 binding molecule comprises the AME 5 Fv or Fab. In additional embodiments, the CD20 binding molecule comprises an Fv or Fab selected from the group consisting of AME 21E1 Hum, AME 6F1, AME 2C2, AME 1D10, AME 15, AME 18, AME 5-3, AME 1C2, and AME 4H5.

In particular embodiments, the present invention provides fusion constructs comprising a CD20 binding molecule (e.g. an antibody or antibody fragment) and a fusion partner, such as an enzyme, detectable label, carbohydrate molecule, a lipid, etc. In some embodiments, the fusion construct comprises an Fab or Fab'2 that binds human CD20 and an enzyme for converting a pro-drug into an active form.

In certain embodiments, the CD20 binding molecule is contained within a host cell (e.g. eukaryotic, or prokaryotic host cell). In other embodiments, the nucleic acid sequence encoding the light and/or heavy chain is contained within a plasmid or other expression vector.

In some embodiments, the present invention provides compositions comprising a CD20 binding molecule that has a binding affinity ($K_d$) for human CD20 of $5.0 \times 10^{-10}$ M or less (e.g., $5.0 \times 10^{-10}$ M-$5.0 \times 10^{-11}$ M). In other embodiments, the present invention provides compositions comprising a CD20 binding molecule, wherein the CD20 binding molecule has a binding affinity ($K_d$) for human CD20 of $5.0 \times 10^{-10}$ M or less, and a dissociation rate (koff) for human CD20 of $5.0 \times 10^{-4}$ s$^{-1}$ or less.

In additional embodiments, the CD20 binding molecule has a binding affinity ($K_d$) for human CD20 of $1.5 \times 10^{-10}$ M or less. In some embodiments, the CD20 binding molecule has a binding affinity ($K_d$) for human CD20 of $1.0 \times 10^{-10}$ M or less. In certain embodiments, the CD20 binding molecule has a dissociation rate (koff) for human CD20 of $2.5 \times 10^{-4}$ s$^{-1}$ or less. In particular embodiments, the CD20 binding molecule has a dissociation rate (koff) for human CD20 of $1.0 \times 10^{-4}$ s$^{-1}$ or less (e.g., $1.0 \times 10^{-4}$ s$^{-1}$-$1.0 \times 10^{-5}$ s$^{-1}$). In some embodiments, the CD20 binding molecule has a dissociation rate (koff) for human CD20 of $8.0 \times 10^{-5}$ s$^{-1}$ or less. In further embodiments, the CD20 binding molecule has an association rate (kon) for human CD20 of $1.0 \times 10^{5}$ M$^{-1}$ s$^{-1}$ or greater (e.g., $1.0 \times 10^{5}$ M$^{-1}$ s$^{-1}$-$1.0 \times 10^{6}$ M$^{-1}$ s$^{-1}$.) In certain embodiments, the CD20 binding molecule has an association rate (kon) for human CD20 of $5.0 \times 10^{5}$ M$^{-1}$ s$^{-1}$ or greater.

In some embodiments, the present invention provides methods of treating B cell lymphoma comprising: a) providing; i) a subject, and ii) a composition, wherein the composition comprises a CD20 binding molecule of the present invention; and b) administering the composition to the subject. In other embodiments, the present invention provides methods of treating a disease comprising: a) providing; i) a subject with symptoms of the disease, and ii) a composition, wherein the composition comprises the CD20 binding molecules of the present invention; and b) administering the composition to the subject such that the symptoms are reduced or eliminated. In particular embodiments, the disease is selected from the group consisting of: relapsed Hodgkin's disease, resistant Hodgkin's disease high grade, low grade and intermediate grade non-Hodgkin's lymphomas (NHLs), B cell chronic lymphocytic leukemia (B-CLL), lymphoplasmacytoid lymphoma (LPL), mantle cell lymphoma (MCL), follicular lymphoma (FL), diffuse large cell lymphoma (DLCL), Burkitt's lymphoma (BL), AIDS-related lymphomas, monocytic B cell lymphoma, angioimmunoblastic lymphoadenopathy, small lymphocytic; follicular, diffuse large cell; diffuse small cleaved cell; large cell immunoblastic lymphoblastoma; small, non-cleaved; Burkitt's and non-Burkitt's; follicular, predominantly large cell; follicular, predominantly small cleaved cell; and follicular, mixed small cleaved and large cell lymphomas.

In some embodiments, the present invention provides a method of treating a disease (e.g. cancer) in an animal requiring such treatment, which method comprises administering the animal an effective amount of the CD20 binding molecules of the present invention. In certain embodiments, the present invention provides the CD20 binding molecules of the present invention for use as a medicament. In other embodiments, the present invention provides the CD20 binding molecules of the present invention in the manufacture of a medicament for the treatment of disease (e.g. NHL). In particular embodiments, the present invention provides a pharmaceutical for the treatment of a disease (e.g. cancer) characterized in that it contain the CD20 binding molecules of the present invention as an active substance.

In preferred embodiments, the subject (patient) is non-immunosuppressed. For example, the patient may have a disease such as systemic lupus erythematosus (SLE). Preferably, once the non-immunosuppressed subject is administered the CD20 binding molecules, no (or negligible) HACA response (human anti-chimeric antibody response) is generated. In certain embodiments, the dosage administered to the subject is about 375 mg/m$^2$ per week for four weeks (without generating a HACA response). In some embodiments, the dosage administered is about 50-300 mg/m$^2$ per week, or about 100-200 mg/m$^2$ per week, for four weeks (e.g. for treating Chronic Lymphocytic Leukemia (CLL)).

In some embodiments, the present invention provides methods of treating B cell lymphoma comprising: a) providing; i) a subject, and ii) a composition, wherein the composition comprises CD20 binding molecules that have a binding affinity ($K_d$) for human CD20 of $5.0 \times 10^{-10}$ M or less, and a dissociation rate (koff) for human CD20 of $5.0 \times 10^{-4}$ s$^{-1}$ or less; and b) administering the composition to the subject.

In certain embodiments, the present invention provides methods for depleting peripheral B cells in a subject in need of such treatment comprising: a) providing; i) a subject, and ii) a composition, wherein the composition comprises CD20 binding molecules that have a binding affinity ($K_d$) for human CD20 of $5.0 \times 10^{-10}$ M or less, and a dissociation rate (koff) for human CD20 of $5.0 \times 10^{-4}$ s$^{-1}$ or less; and b) administering the composition to the subject.

In some embodiments, the light chain variable region comprises a fully human framework. In other embodiments, the light chain variable region comprise a human germline framework. In particular embodiments, the light chain variable region comprises an amino acid sequence selected from SEQ ID NO:59 and 63. In certain embodiments, the heavy chain variable region comprises a fully human framework. In other embodiments, the heavy chain variable region comprises a human germline framework. In additional embodiments, the heavy chain variable region comprises an amino acid sequence selected from 61 and 65.

In some embodiments, the CD20 binding molecule comprises an antibody or antibody fragment (e.g., Fv, Fab, etc.). In particular embodiments, the CD20 binding molecule comprises the AME 33 Fv or Fab. In other embodiments, the CD20 binding molecule comprises the AME 5 Fv or Fab. In additional embodiments, the CD20 binding molecule comprises an Fv or Fab selected from the group consisting of AME 21E1 Hum, AME 6F1, AME 2C2, AME 1D10, AME 15, AME 18, AME 5-3, AME 1C2, AME 4H5.

In other embodiments, the CD20 binding molecule mediates antibody-dependent cell mediated cytotoxicity (ADCC) at approximately the same EC50 level as the C2B8 antibody.

In further embodiments, the CD20 binding molecule mediates antibody-dependent cell mediated cytotoxicity (ADCC), with human peripheral blood mononuclear cells as effectors and B lymphoma cells as targets, at approximately the same EC50 level as the C2B8 antibody. In some embodiments, the CD20 binding molecule mediates antibody-dependent cell mediated cytotoxicity (ADCC) at approximately 1.5 to 2.0 times that of the EC50 level as the C2B8 antibody (the C2B8 antibody is deposited with the ATCC as number 69119). In additional embodiments, the CD20 binding molecule mediates antibody-dependent cell mediated cytotoxicity (ADCC), with human peripheral blood mononuclear cells as effectors and B lymphoma cells as targets, at approximately 1.5 to 2.0 times the EC50 level as the C2B8 antibody. In further embodiments, the CD20 binding molecule mediates antibody-dependent cell mediated cytotoxicity (ADCC) at an EC50 level 10 times that of the C2B8 antibody or greater. In additional embodiments, the CD20 binding molecule mediates antibody-dependent cell mediated cytotoxicity (ADCC), with human peripheral blood mononuclear cells as effectors and B lymphoma cells as targets, at an EC50 level 10 times that of the C2B8 antibody or greater.

In some embodiments, the CD20 binding molecules comprise a human germline light chain framework. In certain embodiments, this light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6.

In other embodiments, the CD20 binding molecules comprise a human germline heavy chain framework. In particular embodiments, this heavy chain human germline framework is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-3, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81.

In some embodiments, the CD20 binding molecule is a CD20 binding peptide or polypeptide. In certain embodiments, the CD20 binding peptide comprises an anti-CD20 antibody or anti-CD20 antibody fragment (e.g., Fv, Fab, F(ab')$_2$, etc). In other embodiments, the peptide comprises a light and/or heavy chain variable region. In particular embodiments, the light chain variable region and/or heavy chain variable region comprises a framework region or at least a portion of a framework region (e.g. containing 2 or 3 subregions, such as FR2 and FR3). In certain embodiments, at least FRL1, FRL2, FRL3, or FRL4 is fully human. In other embodiments, at least FRH1, FRH2, FRH3, or FRH4 is fully human. In some embodiments, at least FRL1, FRL2, FRL3, or FRL4 is a germline sequence (e.g. human germline). In other embodiments, at least FRH1, FRH2, FRH3, or FRH4 is a germline sequence (e.g. human germline). In preferred embodiments, the framework region is a fully human framework region. In some embodiments, the framework region comprises SEQ ID NO: 71, 72, 73, 74, 79, 80, 81, 82, or combinations thereof. In other embodiments, the framework region comprises SEQ ID NO: 87, 88, 89, 90, 95, 96, 97, 98, or combinations thereof.

In some embodiments, the present invention provides a computer readable medium that encodes a representation of a nucleic acid or amino acid sequence selected from SEQ ID NOs: 1-70, or the complement thereof. In certain embodiments, the representation of these sequences, when delivered to a computer processor, may be displayed to a user (e.g., over the internet).

In certain embodiments, the present invention provides nucleic acid sequences that hybridize (under low, medium or high stringency conditions) to the nucleic acid sequences found in SEQ ID NOs:1-70, or the nucleic acid sequences encoding the amino acid sequences found in SEQ ID NOs: 1-70.

In some embodiments, the present invention provides the complement of the nucleic acid sequences described herein (see e.g. Tables 1-2, and FIGS. 2, 3, 4, 5, 6, and 7). In some embodiments, the present invention provides sequences that hybridize under high, medium or low stringency with the nucleic acid sequences described herein (see e.g. Tables 1-2, and FIGS. 2, 3, 4, 5, 6, and 7).

In certain embodiments, the affinity constant ($K_d$) and association rate (Kon) are determined in a IgG cell binding assay (i.e. cells expressing human CD20 on their surface), using KinExa equilibrium software (e.g. from Sapidyne Instruments, Boise, Id.). In some embodiments, the affinity constant and association rate constant are determined by a kinetic exclusion assay (See, e.g., Chiu et al., (2001) Anal. Chem., 73:5477-5484; Blake, et al., (1996) Journal of Biological Chemistry, 271:27677-27685; Hongo, et al., (2000) Hybridoma, 19:303-315; Khosraviani, et al., (2000) Bioconjugate Chemistry, 11:267-277; and Powers, et al., (2001) Journal of Immunological Methods, 251:123-135, all of which are herein incorporated by reference). In particular embodiments, the kinetic exclusion assay is performed with a KinExA instrument (e.g., KinExA™3000 from Sapidyne Instruments, Boise, Id.), or similar device.

In other embodiments, the CD20 binding molecule comprises a Fab, and further comprises one or more constant regions (e.g., CH2 and/or CH3, see FIGS. 6-7). In particular embodiments, the CD20 binding molecule comprises an antibody (e.g., an antibody comprising a fully human framework with synthetic CDR sequences). In certain embodiments, the antibody comprises an altered (e.g., mutated) Fc region. For example, in some embodiments, the Fc region has been altered to reduce or enhance the effector functions of the antibody. In some embodiments, the Fc region is an isotype selected from IgM, IgA, IgG, IgE, or other isotype.

In some embodiments, amino acid modification(s) are introduced into the CH2 domain of an Fc region of a CD20 binding molecule. Useful amino acid positions for modification in order to generate a variant IgG Fc region with altered Fc gamma receptor (FcγR) binding affinity or activity include any one or more of the following amino acid positions: 268, 269, 270, 272, 276, 278, 280, 283, 285, 286, 289, 290, 292, 293, 294, 295, 296, 298, 300, 301, 303, 305, 307, 309, 331, 333, 334, 335, 337, 338, 340, 360, 373, 376, 416, 419, 430, 434, 435, 437, 438 or 439 of the Fc region of a CD20 binding molecule. In preferred embodiments, the parent Fc region used as the template to generate such variants comprises a human IgG Fc region. In some embodiments, to generate an Fc region variant with reduced binding to the FcγR one may introduce an amino acid modification at any one or more of the following amino acid positions: 252, 254, 265, 268, 269, 270, 272, 278, 289, 292, 293, 294, 295, 296, 298, 300, 301, 303, 322, 324, 327, 329, 333, 335, 338, 340, 373, 376, 382, 388, 389, 414, 416, 419, 434, 435, 437, 438 or 439 of the Fc region of a CD20 binding molecule. In particular embodiments, Fc region variants with improved binding to one or more FcγRs may also be made. Such Fc region variants may comprise an amino acid modification at any one or more of the following amino acid positions: 280, 283, 285, 286, 290, 294, 295, 298, 300, 301, 305, 307, 309, 312, 315, 331, 333, 334, 337, 340, 360, 378, 398 or 430 of the Fc region of a CD20 binding molecule. In certain embodiments, the amino acid modification is Y300I.

In other embodiments, the amino acid modification is Y300L. In some embodiments, the amino acid modification is Q295K or Q295L. In certain embodiments, the amino acid modification is E294N. In other embodiments, the amino acid modification at position 296 is Y296P. In some embodiments, the amino acid modification at position 298 is S298P. In other embodiments, the amino acid modification is S298N, S298P, S298V or S298D.

In certain embodiments, the CD20 binding molecule comprises a heavy chain constant region mutation. In other embodiments, the CD20 binding molecule comprises a heavy chain constant region with a mutation selected from D280H and K290S.

Alternatively or additionally, it may be useful to combine amino acid modifications with one or more further amino acid modifications that alter C1q binding and/or the complement dependent cytotoxicity function of the Fc region of a CD20 binding molecule. The starting polypeptide of particular interest may be one that binds to C1q and displays complement dependent cytotoxicity (CDC). Amino acid substitutions described herein may serve to alter the ability of the starting polypeptide to bind to C1q and/or modify its complement dependent cytotoxicity function (e.g., to reduce and preferably abolish these effector functions). However, polypeptides comprising substitutions at one or more of the described positions with improved C1q binding and/or complement dependent cytotoxicity (CDC) function are contemplated herein. For example, the starting polypeptide may be unable to bind C1q and/or mediate CDC and may be modified according to the teachings herein such that it acquires these further effector functions. Moreover, polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO0042072, which is hereby incorporated by reference.

As disclosed above, one can design an Fc region of a CD20 binding molecule with altered effector function, e.g., by modifying C1q binding and/or FcγR binding and thereby changing CDC activity and/or ADCC activity. For example, one can generate a variant Fc region of a CD20 binding molecule with improved C1q binding and improved FcγRIII binding (e.g., having both improved ADCC activity and improved CDC activity).

Alternatively, where one desires that effector function be reduced or ablated, one may engineer a variant Fc region with reduced CDC activity and/or reduced ADCC activity. In other embodiments, one may increase only one of these activities, and optionally also reduce the other activity (e.g., to generate an Fc region variant with improved ADCC activity, but reduced CDC activity and vice versa).

Fc mutations can also be introduced in the CD20 binding molecules of the present invention to alter their interaction with the neonatal Fc receptor (FcRn) and improve their pharmacokinetic properties. Several experiments suggest that the interaction between the Fc region of an antibody and the FcRn plays a role in the persistence of immunoglobulins in serum. For instance, an unusually short serum half-life is observed for IgG molecules in mice that lack a functional FcRn. Fc mutations that improve binding to the FcRn appear to prolong serum half-life and, conversely, mutations in the rat FcRn that result in tighter IgG binding also improve serum half-life. A collection of human Fc variants with improved binding to the FcRn has also been described (Shields et al., (2001) High resolution mapping of the binding site on human IgGI for FcγRI, FcγR11, FcγRIII, and FcRn and design of IgG1 variants with improved binding to the FcγR, J. Biol. Chem. 276: 6591-6604). It has been reported that the increased binding affinity of IgG molecules for the FcRn observed at low pH (e.g., during pinocytosis or fluid phase endocytosis of IgG molecules from serum) impacts serum half-life (Ghetie et al., (1997) Increasing the serum persistence of an IgG fragment by random mutagenesis, Nat. Biotechnol. 15:637-640; Medesan et al., (1998) Comparative studies of rat IgG to further delineate the Fc:FcRn interaction site. Eur. J. Immunol. 28:2092-2100; Kim et al., (1999) Mapping the site on human IgG for binding of the MHC class I-related receptor, FcRn, Eur. J. Immunol. 29:2819-2825; Dall'Acqua et al., (2002) Increasing the affinity of a human IgGI for the neonatal Fc receptor: biological consequences, J. Immunol. 169: 5171-5180). However, mutations that increase binding at high pH appear to adversely affect serum half-life (Dall'Acqua et al., (2002) Increasing the affinity of a human IgG1 for the neonatal Fc receptor: biological consequences, J. Immunol. 169:5171-5180). All of the articles above are herein incorporated by reference. Therefore, Fc mutations could be introduced in the CD20 binding molecules of the present invention in order to increase their affinity for the FcRn at low pH but maintain or decrease their affinity for the FcRn at higher pH.

Another type of amino acid substitution serves to alter the glycosylation pattern of the Fc region of a CD20 binding molecule. This may be achieved, for example, by deleting one or more glycosylation site(s) found in the polypeptide, and/or adding one or more glycosylation sites that are not present in the polypeptide. Glycosylation of an Fc region is typically either N-linked or O-linked. N-linked refers to the attachment of the carbohydrate moiety to the side chain of an asparagine residue. The peptide sequences asparagine-X-serine and asparagine-X-threonine, where X is any amino acid except proline, are the recognition sequences for enzymatic attachment of the carbohydrate moiety to the asparagine side chain. Thus, the presence of either of these peptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the Fc region of a CD20 binding molecule is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites).

In certain embodiments, the CD20 binding molecules of the present invention are expressed in cells that express beta (1,4)—N-acetylglucosaminyltransferase III (GnT III), such that GnT III adds GlcNAc to the CD20 binding molecules. Methods for producing binding molecules in such a fashion are provided in WO9954342, WO03011878, patent publication 20030003097A1, and Umana et al., Nature Biotechnology, 17:176-180, February 1999; all of which are herein specifically incorporated by reference in their entireties.

In certain embodiments, the present invention provides kits comprising: a) a CD20 binding molecule of the present invention; and b) instructions for using the CD20 binding molecule to treat a disease in a subject or instructions for employing the CD20 binding molecule for scientific research or diagnostic purposes (e.g., for performing ELISA assays, etc.). In some embodiments, the present invention provides cell lines stably or transiently transfected with nucleic acid sequences encoding the CD20 binding molecules of the present invention.

DESCRIPTION OF THE FIGURES

FIG. 2A shows the amino acid sequence of the light chain variable region of AME 33 (SEQ ID NO:59), and FIG. 2B shows the nucleic acid sequence of the light chain variable region of AME 33 (SEQ ID NO:60).

FIG. 3A shows the amino acid sequence of the heavy chain variable region of AME 33 (SEQ ID NO:61), and FIG. 3B shows the nucleic acid sequence of the heavy chain variable region of AME 33 (SEQ ID NO:62).

FIG. 4A shows the amino acid sequence of the light chain variable region of AME 5 (SEQ ID NO:63), and FIG. 4B shows the nucleic acid sequence of the light chain variable region of AME 5 (SEQ ID NO:64).

FIG. 5A shows the amino acid sequence of the heavy chain variable region of AME 5 (SEQ ID NO:65), and FIG. 5B shows the nucleic acid sequence of the heavy chain variable region of AME 5 (SEQ ID NO:66).

FIG. 6A shows the complete amino acid sequence of the light chain of AME 33 (SEQ ID NO:67), and FIG. 6B shows the complete nucleic acid sequence of the light chain of AME 33 (SEQ ID NO:68).

FIG. 7A shows the complete amino acid sequence of the heavy chain of AME 33 (SEQ ID NO:69), and FIG. 7B shows the complete nucleic acid sequence of the heavy chain of AME 33 (SEQ ID NO:70).

FIGS. 8 and 9 show the results of the ELISA binding assay described in Example 2.

FIG. 10 shows the results of the live B lymphoma Fab binding assays described in Example 3.

DEFINITIONS

Figure 1:
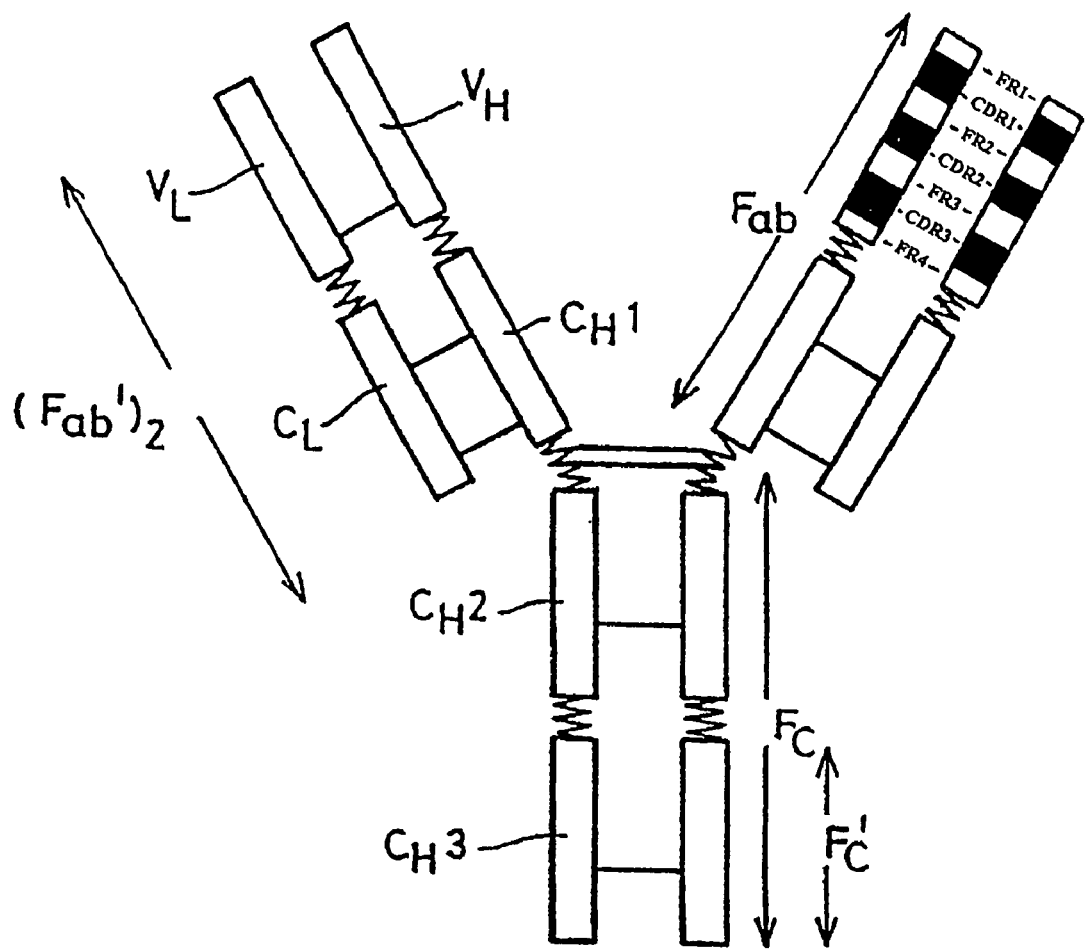
FIG. 1 shows a schematic representation of an IgG molecule with the various regions and sections labeled. The CDRs and framework regions (FR) of one of the two variable region light chains, and one of the two variable region heavy chains, are also labeled.

To facilitate an understanding of the invention, a number of terms are defined below.

The term "antibody," as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3 (see FIG. 1). Each light chain is comprised of a light chain variable region (abbreviated herein as LCVR or VL) and a light chain constant region. The light chain constant region is comprised of one domain, CL (see FIG. 1). The VH and VL regions can be further subdivided into regions of hypervariability, termed complementarity determining regions (CDRs), interspersed with regions that are more conserved, termed framework regions (FR). Each variable region (VH or VL) contains 3 CDRs, designated CDR1, CDR2 and CDR3 (see FIG. 1). Each variable region also contains 4 framework sub-regions, designated FR1, FR2, FR3 and FR4 (see FIG. 1).

As used herein, the term "antibody fragments" refers to a portion of an intact antibody. Examples of antibody fragments include, but are not limited to, linear antibodies, single-chain antibody molecules, Fv, Fab and F(ab')$_2$ fragments, and multispecific antibodies formed from antibody fragments. The antibody fragments preferably retain at least part of the heavy and/or light chain variable region.

As used herein, the terms "complementarity determining region" and "CDR" refer to the regions that are primarily responsible for antigen-binding. There are three CDRs in a light chain variable region (CDRL1, CDRL2, and CDRL3), and three CDRs in a heavy chain variable region (CDRH1, CDRH2, and CDRH3). The residues that make up these six CDRs have been characterized by Kabat and Chothia as follows: residues 24-34 (CDRL1), 50-56 (CDRL2) and 89-97 (CDRL3) in the light chain variable region and 31-35 (CDRH1), 50-65 (CDRH2) and 95-102 (CDRH3) in the heavy chain variable region; Kabat et al., (1991) Sequences of Proteins of Immunological Interest, 5th Ed. Public Health Service, National Institutes of Health, Bethesda, Md., herein incorporated by reference; and residues 26-32 (CDRL1), 50-52 (CDRL2) and 91-96 (CDRL3) in the light chain variable region and 26-32 (CDRH1), 53-55 (CDRH2) and 96-101 (CDRH3) in the heavy chain variable region; Chothia and Lesk (1987) J. Mol. Biol. 196: 901-917, herein incorporated by reference. Unless otherwise specified, the terms "complementarity determining region" and "CDR" as used herein, include the residues that encompass both the Kabat and Chothia definitions (i.e., residues 24-34 (CDRL1), 50-56 (CDRL2), and 89-97 (CDRL3) in the light chain variable region; and 26-35 (CDRH1), 50-65 (CDRH2), and 95-102 (CDRH3)). Also, unless specified, as used herein, the numbering of CDR residues is according to Kabat.

As used herein, the term "framework" refers to the residues of the variable region other than the CDR residues as defined herein. There are four separate framework sub-regions that make up the framework: FR1, FR2, FR3, and FR4 (See FIG. 1). In order to indicate if the framework sub-region is in the light or heavy chain variable region, an "L" or "H" maybe added to the sub-region abbreviation (e.g., "FRL1" indicates framework sub-region 1 of the light chain variable region). Unless specified, the numbering of framework residues is according to Kabat. It is noted that, in certain embodiments, the CD20 binding molecules of the present invention may have less than a complete framework (e.g. the CD20 binding molecule may have a portion of a framework that only contains one or more of the four sub-regions).

As used herein, the term "fully human framework" means a framework with an amino acid sequence found naturally in humans. Examples of fully human frameworks, include, but are not limited to, KOL, NEWM, REI, EU, TUR, TEI, LAY and POM (See, e.g., Kabat et al., (1991) Sequences of Proteins of Immunological Interest, US Department of Health and Human Services, NIH, USA; and Wu et al., (1970) J. Exp. Med. 132, 211-250, both of which are herein incorporated by reference).

As used herein, the terms "subject" and "patient" refer to any animal, such as a mammal like a dog, cat, bird, livestock, and preferably a human.

As used herein, the term "codon" or "triplet" refers to a group of three adjacent nucleotide monomers which specify one of the naturally occurring amino acids found in polypeptides. The term also includes codons which do not specify any amino acid. It is also noted that, due to the degeneracy of the genetic code, there are many codons that code for the same amino acid. As such, many of the bases of the nucleic acid sequences of the present invention (see, e.g., Tables 1 and 2) can be changed without changing the actual amino acid sequence that is encoded. The present invention is intended to encompass all such nucleic acid sequences.

As used herein, the terms "an oligonucleotide having a nucleotide sequence encoding a polypeptide," "polynucleotide having a nucleotide sequence encoding a polypeptide," and "nucleic acid sequence encoding a peptide" means a nucleic acid sequence comprising the coding region of a particular polypeptide. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc., or a combination of both endogenous and exogenous control elements.

Also, as used herein, there is no size limit or size distinction between the terms "oligonucleotide" and "polynucleotide." Both terms simply refer to molecules composed of nucleotides. Likewise, there is no size distinction between the terms "peptide" and "polypeptide." Both terms simply refer to molecules composed of amino acid residues.

As used herein, the terms "complementary" or "complementarity" are used in reference to polynucleotides (i.e., a sequence of nucleotides) related by the base-pairing rules. For example, the sequence "5'-A-G-T 3", is complementary to the sequence "3-T-C-A-5'". Complementarity may be "partial", in which only some of the nucleic acids' bases are matched according to the base pairing rules, or, there may be "complete" or "total" complementarity between the nucleic acids. The degree of complementarity between nucleic acid strands has significant effects on the efficiency and strength of hybridization.

As used herein, the term "the complement of" a given sequence is used in reference to the sequence that is completely complementary to the sequence over its entire length. For example, the sequence 5'-A-G-T-A-3' is "the complement" of the sequence 3'-T-C-A-T-5'. The present invention also provides the complement of the sequences described herein (e.g., the complement of the nucleic acid sequences in SEQ ID NOs: 1-70).

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent [50×Denhardt's contains per 500 ml: 5 g Ficoll (Type 400, Pharmacia), 5 g BSA (Fraction V; Sigma)] and 100 μg/ml denatured salmon sperm DNA, followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE, 0.5% SDS, 5×Denhardt's reagent and 100 μg/ml denatured salmon sperm DNA, followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE, 0.1% SDS, 5×Denhardt's reagent and 100 g/ml denatured salmon sperm DNA, followed by washing in a solution comprising 5×SSPE, 0.1% SDS at 42° C. when a probe of about 500 nucleotides in length is employed.

The term "isolated" when used in relation to a nucleic acid, as in "an isolated oligonucleotide" or "isolated polynucleotide" or "isolated nucleic acid sequence encoding a CD20 binding molecule" (see, e.g., Tables 1-2) refers to a nucleic acid sequence that is identified and separated from at least one contaminant nucleic acid with which it is ordinarily associated (e.g. host cell proteins).

As used herein, the terms "portion" when used in reference to a nucleotide sequence (as in "a portion of a given nucleotide sequence") refers to fragments of that sequence. The fragments may range in size from ten nucleotides to the entire nucleotide sequence minus one nucleotide (e.g., 10 nucleotides, 20, 30, 40, 50, 100, 200, etc.).

As used herein, the term "portion" when in reference to an amino acid sequence (as in "a portion of a given amino acid sequence") refers to fragments of that sequence. The fragments may range in size from six amino acids to the entire amino acid sequence minus one amino acid (e.g., 6 amino acids, 10, 20, 30, 40, 75, 200, etc.).

As used herein, the term "purified" or "to purify" refers to the removal of contaminants from a sample. For example, CD20 specific antibodies may be purified by removal of contaminating non-immunoglobulin proteins; they are also purified by the removal of immunoglobulins that do not bind to the same antigen. The removal of non-immunoglobulin proteins and/or the removal of immunoglobulins that do not bind the particular antigen results in an increase in the percentage of antigen specific immunoglobulins in the sample. In another example, recombinant antigen-specific polypeptides are expressed in bacterial host cells and the polypeptides are purified by the removal of host cell proteins; the percentage of recombinant antigen-specific polypeptides is thereby increased in the sample.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells such as PER.C6™ (Crucell, The Netherlands) and CHO cells, avian cells, amphibian cells, plant cells, fish cells, and insect cells), whether located in vitro or in vivo. For example, host cells may be located in a transgenic animal.

As used herein, the terms "computer memory" and "computer memory device" refer to any storage media readable by a computer processor. Examples of computer memory include, but are not limited to, RAM, ROM, computer chips, digital video discs (DVDs), compact discs (CDs), hard disk drives (HDD), and magnetic tapes.

As used herein, the term "computer readable medium" refers to any device or system for storing and providing information (e.g., data and instructions) to a computer processor. Examples of computer readable media include, but are not limited to, DVDs, CDs, hard disk drives, magnetic tapes and servers for streaming media over networks.

As used herein, the phrase "computer readable medium encodes a representation" of a nucleic acid or amino acid sequence, refers to computer readable medium that has stored thereon information, that when delivered to a processor, allows the nucleic or amino acid sequence to be displayed to a user (e.g., printed out or presented on a display screen).

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "Fc region" refers to a C-terminal region of an immunoglobulin heavy chain (e.g., as shown in FIG. 1). The "Fc region" may be a native sequence Fc region or a variant Fc region (e.g., with increased or decreased effector functions).

As used herein, an Fc region may possess "effector functions" that are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g. Fc binding assays, ADCC assays, CDC assays, etc.).

As used herein, an "isolated" peptide, polypeptide, or protein is one that has been identified and separated and/or recovered from a component of its natural environment. Contaminant components of its natural environment are materials that would interfere with diagnostic or therapeutic uses for the polypeptide, and may include enzymes, hormones, and other proteinaceous or non-proteinaceous solutes. In certain embodiments, the isolated polypeptide is purified (1) to greater than 95% by weight of polypeptides as determined by the Lowry method, and preferably, more than 99% by weight, (2) to a degree sufficient to obtain at least 15 residues of N-terminal or internal amino acid sequence by use of a spinning cup sequenator, or (3) to homogeneity by SDS-page under reducing or nonreducing conditions using Coomassie blue, or silver stain. An isolated polypeptide includes the polypeptide in situ within recombinant cells since at least one component of the polypeptide's natural environment will not be present. Ordinarily, however, an isolated polypeptide will be prepared by a least one purification step.

As used herein, the term "treatment" refers to both therapeutic treatment and prophylactic or preventative measures. Those in need of treatment include those already with the disorder as well as those in which the disorder is to be prevented.

The phrase "under conditions such that the symptoms are reduced" refers to any degree of qualitative or quantitative reduction in detectable symptoms of any disease treatable by CD20 binding molecules, including but not limited to, a detectable impact on the rate of recovery from disease (e.g., rate of weight gain), or the reduction of at least one of the symptoms normally associated with the particular disease.

The term "human CD20" (abbreviated herein as hCD20), as used herein, is intended to refer to the human B lymphocyte-restricted differentiation antigen (also known as Bp35). CD20 is expressed during early pre-B cell development and remains until plasma cell differentiation. The CD20 molecule may regulate a step in the activation process which is required for cell cycle initiation and differentiation, and is usually expressed at very high levels on neoplastic B cells. CD20 is present on both "normal" B cell as well as "malignant" B cells (i.e. those B cells whose unabated proliferation can lead to B cell lymphoma).

The terms "affinity", "binding affinity" and "$K_d$" refer to the equilibrium dissociation constant (expressed in units of concentration) associated with each CD20 binding molecule-CD20 protein complex. The binding affinity is directly related to the ratio of the off-rate constant (generally reported in units of inverse time, e.g., seconds$^{-1}$) to the on-rate constant (generally reported in units of concentration per unit time, e.g., molar/second). The binding affinity may be determined by, for example, an ELISA assay, kinetic exclusion assay or surface plasmon resonance. It is noted that certain epitopes can occur repetitively (multivalent) on a cell surface and that the dissociation constant (koff) for the binding of an antibody to a repetitive epitope may be greatly diminished over the dissociation constant for the reaction of the same antibody with the corresponding ligand in univalent form. The diminished dissociation constant arises because when one antibody-ligand bond dissociates, other bonds hold the bivalent (or multivalent) antibody to the multivalent ligand, allowing the dissociated bond to form again. The dissociation constant for the reaction between bivalent (or multivalent) Ab and multivalent ligand has been termed the functional affinity to contrast it with intrinsic affinity, which is the association constant for an antibodies representative individual site.

The terms "dissociation", "dissociation rate" and "$k_{off}$" as used herein, are intended to refer to the off rate constant for dissociation of a CD20-binding molecule from the antibody/antigen complex.

The terms "association", "association rate" and "$k_{on}$" as used herein, are intended to refer to the on rate constant for association of a CD20 binding molecule with an antigen to form an antibody/antigen complex.

The terms "effective concentration" and "$EC_{50}$" as used herein, are intended to refer to the concentration of a CD20 binding molecule capable of interacting with sufficient quantities of CD20 molecules to produce an effect on approximately 50% of the treated cells.

DESCRIPTION OF THE INVENTION

The present invention provides CD20 binding molecules and nucleic acid sequences encoding CD20 binding molecules. In particular, the present invention provides CD20 binding molecules with a high binding affinity, and a low dissociation rate, with regard to human CD20. Preferably, the CD20 binding molecules of the present invention comprise light and/or heavy chain variable regions with fully human frameworks (e.g. human germline frameworks). The description of the invention is divided into the following sections below for convenience: I. CD20 Binding Molecules; II. Generating CD20 Binding Molecules; III. Therapeutic Formulations and Uses; and IV. Additional CD20 Binding Molecule Uses.

I. CD20 Binding Molecules

The present invention provides CD20 binding molecules with desirable characteristics. In particular, in some embodiments, the CD20 binding molecules have a high binding affinity ($K_d$) with regard to human CD20. In certain embodiments, the CD20 binding molecules have a low dissociation rate ($k_{off}$) with regard to human CD20. In preferred embodiments, the CD20α binding molecules of the present invention have a high binding affinity, a low dissociation rate and are effective at low concentrations. While not necessary to practice or understand the invention, it is believed that the CD20 binding molecules of the present invention, with high binding affinity, and a low dissociation rate, are particularly well suited for therapeutic use in humans and are less likely to elicit a HACA response than other anti-CD20 molecules, such as RITUXAN(C2B8).

In further embodiments, the CD20 binding molecules of the present invention bind human CD20. In other embodiments, the CD20 binding molecules of the present invention CD20 on the surface of B cells from Cynomolgus macaques.

In preferred embodiments, the CD20 binding molecules of the present invention comprise a light and/or heavy chain variable region, preferably having a fully human framework. In particularly preferred embodiments, the CD20 binding molecules of the present invention comprise a light and/or heavy chain variable region, preferably having a human germline framework. While not necessary to practice or understand the invention, it is believed that the CD20 binding molecules of the present invention (see, e.g. the Examples below) will illicit very little or no immunogenic response when administered to a human (e.g. to treat a disease), as the framework regions may be fully human.

As described below in Tables 1 and 2, the present invention provides numerous CDRs useful for generating CD20 binding molecules. For example, one or more of the CDRs shown can be combined with a framework sub-region (e.g., a fully human FR1, FR2, FR3, or FR4) in order to generate a CD20 binding peptide, or a nucleic acid sequence encoding a CD20 binding peptide. Also, the CDRs shown in the Tables below may be combined, for example, such that three CDRs are present in a light chain variable region, and/or three CDRs are present in a heavy chain variable region.

The CDRs shown below may be inserted into a human framework (e.g., by recombinant techniques) into the light and heavy chain frameworks in order to generate CD20 binding molecules or nucleic acid sequences encoding CD20 binding molecules. For example, the CDRL1 could be replaced by SEQ ID NO: 1, 3, 5, 7, 9, 11, 13, 15, 17, 19, or 21 as shown in Table 1. Likewise, the CDRL1 could be replaced by SEQ ID NO: 2, 4, 6, 8, 10, 12, 14, 16, 18, 20, or 22 as shown in Table 1. This same procedure may be used with all of the CDRs shown in Tables 1-2. Tables 1 and 2 shown immediately below.

TABLE 1

Light Chain CDRs

| SEQ ID NO | CDR Name* | Sequence |
|---|---|---|
| SEQ ID NO: 1 | CDRL1 | RASSSVSYIH |
| SEQ ID NO: 2 | CDRL1 | AGGGCCAGCTCAAGTGTAAGTTACATCCAC |
| SEQ ID NO: 3 | CDRL1 | RASSSVHYIH |
| SEQ ID NO: 4 | CDRL1 | AGGGCCAGCTCAAGTGTACATTACATCCAC |
| SEQ ID NO: 5 | CDRL1 | RASSSVPYIH |
| SEQ ID NO: 6 | CDRL1 | AGGGCCAGCTCAAGTGTACCGTACATCCAC |
| SEQ ID NO: 7 | CDRL2 | ATSNLAS |
| SEQ ID NO: 8 | CDRL2 | GCCACATCCAACCTGGCTTCT |
| SEQ ID NO: 9 | CDRL2 | ATTNLAT |
| SEQ ID NO: 10 | CDRL2 | GCCACAACCAACCTGGCTACG |
| SEQ ID NO: 11 | CDRL2 | ATSGLAS |
| SEQ ID NO: 12 | CDRL2 | GCCACATCCGGCCTGGCTTCT |
| SEQ ID NO: 13 | CDRL2 | ATSALAS |
| SEQ ID NO: 14 | CDRL2 | GCCACATCCGCTCTGGCTTCT |
| SEQ ID NO: 15 | CDRL3 | QQWTSNPPT |
| SEQ ID NO: 16 | CDRL3 | CAGCAGTGGACTAGTAACCCACCCACG |
| SEQ ID NO: 17 | CDRL3 | QQWTFNPPT |
| SEQ ID NO: 18 | CDRL3 | CAGCAGTGGACTTTTAACCCACCCACG |
| SEQ ID NO: 19 | CDRL3 | QQWLSNPPT |
| SEQ ID NO: 20 | CDRL3 | CAGCAGTGGCTGAGTAACCCACCCACT |
| SEQ ID NO: 21 | CDRL3 | QTWTFNPPT |
| SEQ ID NO: 22 | CDRL3 | CAGACTTGGACTTTTAACCCTCCCACG |

*The work of Kabat was used to number residues. CDRs include Kabat and Chothia residues.

TABLE 2

Heavy Chain CDRs

| SEQ ID NO | CDR Name* | Sequence |
|---|---|---|
| SEQ ID NO: 23 | CDRH1 | GYTFTSYNMH |
| SEQ ID NO: 24 | CDRH1 | GGATACACCTTCACCAGCTACAATATGCAC |
| SEQ ID NO: 25 | CDRH1 | GRTFTSYNMH |
| SEQ ID NO: 26 | CDRH1 | GGCCGTACATTTACCAGTTACAATATGCAC |
| SEQ ID NO: 27 | CDRH2 | AIYPGNGDTSYNQKFKG |
| SEQ ID NO: 28 | CDRH2 | GCCATCTATCCTGGAAATGGTGATACAAGCTACAATCAGAAGTTCAAAGGC |
| SEQ ID NO: 29 | CDRH2 | AIYPGNGDTSYNHKHKG |
| SEQ ID NO: 30 | CDRH2 | GCCATCTATCCTGGAAATGGTGATACAAGCTACAATCATAAGCATAAGGG |
| SEQ ID NO: 31 | CDRH2 | AIYPGNGDTSYNQKFKW |
| SEQ ID NO: 32 | CDRH2 | GCCATCTATCCTGGAAATGGTGATACAAGCTACAATCAGAAGTTTAAATGG |
| SEQ ID NO: 33 | CDRH2 | AIYPLNGDTSYNQKFKL |
| SEQ ID NO: 34 | CDRH2 | GCTATTTATCCCTTGAATGGTGATACTTCCTACAATCAGAAGTTCAAACTC |
| SEQ ID NO: 35 | CDRH2 | AIYPLNGDTSYNRKSKL |
| SEQ ID NO: 36 | CDRH2 | GCTATTTATCCCTTGAATGGTGATACTTCCTACAATCGTAAGTCGAAACTC |
| SEQ ID NO: 37 | CDRH2 | AIYPLTGDTSYNQKFKL |
| SEQ ID NO: 38 | CDRH2 | GCTATTTATCCCTTGACGGGTGATACTTCCTACAATCAGAAGTTCAAACTC |
| SEQ ID NO: 39 | CDRH2 | AIYPLTGDTSYNQKSKL |
| SEQ ID NO: 40 | CDRH2 | GCTATTTATCCCTTGACGGGTGATACTTCCTACAATCAGAAGTCGAAACTC |
| SEQ ID NO: 41 | CDRH3 | STYYGGDWYFDV |
| SEQ ID NO: 42 | CDRH3 | TCGACTTACTACGGCGGTGACTGGTACTTCGATGTC |
| SEQ ID NO: 43 | CDRH3 | STYYGGDWQFDV |
| SEQ ID NO: 44 | CDRH3 | TCGACTTACTACGGCGGTGACTGGCAGTTCGACGTC |
| SEQ ID NO: 45 | CDRH3 | STYYGGDWQFDE |
| SEQ ID NO: 46 | CDRH3 | TCGACTTATTACGGCGGTGACTGGCAGTTCGACGAG |
| SEQ ID NO: 47 | CDRH3 | STYYGGDWQFDQ |
| SEQ ID NO: 48 | CDRH3 | TCGACTTATTACGGCGGTGACTGGCAGTTCGACCAG |
| SEQ ID NO: 49 | CDRH3 | STYYGGDWSFDV |
| SEQ ID NO: 50 | CDRH3 | TCGACTTACTACGGCGGTGACTGGAGTTTCGATGTC |
| SEQ ID NO: 51 | CDRH3 | STYYGGDWTFDV |
| SEQ ID NO: 52 | CDRH3 | TCGACTTACTACGGCGGTGACTGGACTTTCGATGTC |
| SEQ ID NO: 53 | CDRH3 | STYVGGDWTFDV |
| SEQ ID NO: 54 | CDRH3 | TCGACTTACGTGGGCGGTGACTGGACTTTCGATGTC |
| SEQ ID NO: 55 | CDRH3 | SYYVGGDWTFDV |
| SEQ ID NO: 56 | CDRH3 | TCGTATTACGTGGGCGGTGACTGGACTTTCGATGTC |
| SEQ ID NO: 57 | CDRH3 | STYVGGDWQFDV |
| SEQ ID NO: 58 | CDRH3 | TCGACTTACGTGGGCGGTGACTGGCAGTTCGATGTC |

*The work of Kabat was used to number residues. CDRs include both Kabat and Chothia residues.

The present invention also provides sequences that are substantially the same as the CDR sequences (both amino acid and nucleic acid) shown in the above Tables. For example, one or two amino acid may be changed in the sequences shown in the Tables. Also for example, a number of nucleotide bases may be changed in the sequences shown in the Tables. Changes to the amino acid sequence may be generated by changing the nucleic acid sequence encoding the amino acid sequence. A nucleic acid sequence encoding a variant of a given CDR may be prepared by methods known in the art using the guidance of the present specification for particular sequences. These methods include, but are not limited to, preparation by site-directed (or oligonucleotide-mediated) mutagenesis, PCR mutagenesis, and cassette mutagenesis of an earlier prepared nucleic acid encoding the CDR. Site-directed mutagenesis is a preferred method for preparing substitution variants. This technique is well known in the art (see, e.g., Carter et al., (1985) Nucleic Acids Res. 13: 4431-4443 and Kunkel (1985) Proc. Natl. Acad. Sci. USA 82: 488-492, both of which are hereby incorporated by reference).

Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the starting CDR (see, e.g., Vallette et. al., (1989) Nucleic Acids Res. 17: 723-733, hereby incorporated by reference). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., (1985) Gene 34: 315-323, hereby incorporated by reference. The starting material is the plasmid (or other vector) comprising the starting CDR DNA to be mutated. The codon(s) in the starting DNA to be mutated are identified. There should be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding a polypeptide variant can be determined, and a nucleic acid sequence encoding such amino acid sequence variant can be generated synthetically. Conservative modifications in the amino acid sequences of the CDRs may also be made. Naturally occurring residues are divided into classes based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Conservative substitutions will entail exchanging a member of one of these classes for another member of the same class. The present invention also provides the complement of the nucleic acid sequences shown in Tables 1 and 2, as well as nucleic acid sequences that will hybridize to these nucleic acid sequences under low, medium, and high stringency conditions.

The CDRs of the present invention may be employed with any type of framework. Preferably, the CDRs are used with fully human frameworks, or framework sub-regions. In particularly preferred embodiments, the frameworks are human germline sequences. Other fully human frameworks or framework sub-regions may also be employed. For example, the NCBI web site contains the sequences for the currently known human framework regions. Examples of human VH sequences include, but are not limited to, VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81, which are provided in Matsuda et al., (1998) J. Exp. Med. 188:1973-1975, that includes the complete nucleotide sequence of the human immunoglobulin chain variable region locus, herein incorporated by reference. Examples of human VK sequences include, but are not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8, which are provided in Kawasaki et al., (2001) Eur. J. Immunol. 31:1017-1028; Schable and Zachau, (1993) Biol. Chem. Hoppe Seyler 374:1001-1022; and Brensing-Kuppers et al., (1997) Gene 191:173-181, all of which are herein incorporated by reference. Examples of human VL sequences include, but are not limited to, V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6, which are provided in Kawasaki et al., (1997) Genome Res. 7:250-261, herein incorporated by reference. Fully human frameworks can be selected from any of these functional germline genes. Generally, these frameworks differ from each other by a limited number of amino acid changes. These frameworks may be used with the CDRs described herein. Additional examples of human frameworks which may be used with the CDRs of the present invention include, but are not limited to, KOL, NEWM, REI, EU, TUR, TEI, LAY and POM (See, e.g., Kabat et al., (1991) Sequences of Proteins of Immunological Interest, US Department of Health and Human Services, NIH, USA; and Wu et al., (1970), J. Exp. Med. 132:211-250, both of which are herein incorporated by reference).

Again, while not necessary to practice or understand the invention, it is believed that the reason the use of germline sequences is expected to help eliminate adverse immune responses in most individuals is as follows. Somatic mutations frequently occur in the variable region of immunoglobulins as a result of the affinity maturation step that takes place during a normal immune response. Although these mutations are predominantly clustered around the hypervariable CDRs, they also impact residues in the framework regions. These framework mutations are not present in the germline genes and are less likely to be immunogenic in patients. In contrast, the general population has been exposed to the vast majority of framework sequences expressed from germline genes and, as a result of immunologic tolerance, these germline frameworks are expected to be less, or non-immunogenic in patients. In order to maximize the likelihood of tolerance, genes encoding the variable regions can be selected from a collection of commonly occurring, functional germline genes, and genes encoding VH and VL regions can be further selected to match known associations between specific heavy and light chains of immunoglobulin molecules.

II. Generating CD20 Binding Molecules

In preferred embodiments, the CD20 binding molecules of the present invention comprise antibodies or antibody fragments (e.g., comprising one or more of the CDRs described herein). An antibody, or antibody fragment, of the present invention can be prepared, for example, by recombinant expression of immunoglobulin light and heavy chain genes in a host cell. For example, to express an antibody recombinantly, a host cell may be transfected with one or more recombinant expression vectors carrying DNA fragments encoding the immunoglobulin light and heavy chains of the antibody such that the light and heavy chains are expressed in the host cell and, preferably, secreted into the medium in which the host cell is cultured, from which medium the antibody can be recovered. Standard recombinant DNA methodologies may be used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel, F. M. et al. (eds.) Current Protocols in Molecular Biology, Greene Publishing Associates, (1989) and in U.S. Pat. No. 4,816,397 by Boss et al., all of which are herein incorporated by reference.

To express an antibody with one or more of the CDRs of the present invention, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see above).

Once the germline VH and VL fragments are obtained, these sequences can be mutated to encode one or more of the CDR amino acid sequences disclosed herein (see, e.g., Tables 1-2). The amino acid sequences encoded by the germline VH and VL DNA sequences may be compared to the CDRs sequence(s) desired to identify amino acid residues that differ from the germline sequences. Then the appropriate nucleotides of the germline DNA sequences are mutated such that the mutated germline sequence encodes the selected CDRs (e.g., the six CDRs that are selected from Tables 1-2), using the genetic code to determine which nucleotide changes should be made. Mutagenesis of the germline sequences may be carried out by standard methods, such as PCR-mediated mutagenesis (in which the mutated nucleotides are incorporated into the PCR primers such that the PCR product contains the mutations) or site-directed mutagenesis. In other embodiments, the variable region is synthesized de novo (e.g., using a nucleic acid synthesizer).

Once DNA fragments encoding the desired VH and VL segments are obtained (e.g., by amplification and mutagenesis of germline VH and VL genes, or synthetic synthesis, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operably linked to another DNA fragment encoding another polypeptide, such as an antibody constant region or a flexible linker. The isolated DNA encoding the VH region can be converted to a full-length heavy chain gene by operably linking the VH-encoding DNA to another DNA molecule encoding heavy chain constant regions (CH1, CH2 and CH3, see, e.g. FIGS. 6-7). The sequences of human heavy chain constant region genes are known in the art (see e.g., Kabat, E. A., et al., (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be, for example, an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operably linked to another DNA molecule encoding only the heavy chain CH1 constant region. In preferred embodiments, the heavy chain constant region is similar to or identical to the constant region shown in FIG. 7.

The isolated DNA encoding the VL region can be converted to a full-length light chain gene (as well as a Fab light chain gene) by operably linking the VL-encoding DNA to another DNA molecule encoding the light chain constant region, CL. The sequences of human light chain constant region genes are known in the art (see e.g., Kabat, E. A., et al., (1991) Sequences of Proteins of immunological Interest, Fifth Edition, U.S. Department of Health and Human Services. NIH Publication No. 91-3242) and DNA fragments encompassing these regions can be obtained by standard PCR amplification. The light chain constant region can be a kappa or lambda constant region, but most preferably is a kappa constant region. In preferred embodiments, the light chain constant region is similar or identical to the constant region shown in FIG. 6.

To create a scFv gene, the VH- and VL-encoding DNA fragments may be operably linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Huston et al., (1988) Proc. Natl. Acad. Sci. USA 85:5879-5883; and McCafferty et al., (1990) Nature 348:552-554), all of which are herein incorporated by reference).

To express the antibodies, or antibody fragments of the invention, DNAs encoding partial or full-length light and heavy chains, (e.g. obtained as described above), may be inserted into expression vectors such that the genes are operably linked to transcriptional and translational control sequences. In this context, the term "operably linked" is intended to mean that an antibody gene is ligated into a vector such that transcriptional and translational control sequences within the vector serve their intended function of regulating the transcription and translation of the antibody gene. The expression vector and expression control sequences are generally chosen to be compatible with the expression host cell used. The antibody light chain gene and the antibody heavy chain gene can be inserted into separate vectors or, more typically, both genes are inserted into the same expression vector. The antibody genes may be inserted into the expression vector by standard methods (e.g., ligation of complementary restriction sites on the antibody gene fragment and vector, or blunt end ligation if no restriction sites are present). Prior to insertion of the light or heavy chain sequences, the expression vector may already carry antibody constant region sequences. For example, one approach to converting the VH and VL sequences to full-length antibody genes is to insert them into expression vectors already encoding heavy chain constant and light chain constant regions, respectively, such that the VH segment is operably linked to the CH segment(s) within the vector and the VL segment is operably linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention may carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; Gene Expression Technology: Methods in Enzymology 185, Academic Press, San Diego, Calif. (1990), herein incorporated by reference. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma virus. For further description of viral regulatory elements, and sequences thereof, see e.g., U.S. Pat. No. 5,168,062 by Stinski, U.S. Pat.

No. 4,510,245 by Cousens et al. and U.S. Pat. No. 4,968,615 by Koszinowski et al., all of which are herein incorporated by reference.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634.665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neomycin gene (for G418 selection).

For expression of the light and heavy chains, the expression vector(s) encoding the heavy and light chains may be transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like.

In certain embodiments, the expression vector used to express the CD20 binding molecules of the present invention are viral vectors, such as retro-viral vectors. Such viral vectors may be employed to generate stably transduced cell lines (e.g. for a continuous source of the CD20 binding molecules). In some embodiments, the GPEX gene product expression technology (from Gala Design, Inc., Middleton, Wis.) is employed to generate CD20 binding molecules (and stable cell lines expressing the CD20 binding molecules). In particular embodiments, the expression technology described in WO0202783 and WO0202738 to Bleck et al. (both of which are herein incorporated by reference in their entireties) is employed.

Preferred mammalian host cells for expressing the recombinant antibodies of the invention include PER.C6™ cells (Crucell, The Netherlands), Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells and SP2 cells. In other preferred embodiments, the host cells express GnT III as described in WO9954342 and U.S. Pat. Pub. 20030003097, both herein incorporated by reference, such that expressed CD20 binding molecules have increased ADCC activity. When recombinant expression vectors encoding antibody genes are introduced into mammalian host cells, the antibodies are generally produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It will be understood that variations on the above procedure are within the scope of the present invention. For example, it may be desirable to transfect a host cell with DNA encoding either the light chain or the heavy chain of an antibody of this invention. Recombinant DNA technology may also be used to remove some or all of the DNA encoding either or both of the light and heavy chains that is not necessary for binding to hCD20. The molecules expressed from such truncated DNA molecules are also encompassed by the antibodies of the invention. In addition, bi-functional antibodies may be produced in which one heavy and one light chain are an antibody of the invention and the other heavy and light chain are specific for an antigen other than hCD20 (e.g., by crosslinking an antibody of the invention to a second antibody by standard chemical crosslinking methods).

In one preferred system for recombinant expression of an antibody, or fragment thereof, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operably linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector may also carry a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

In certain embodiments, the antibodies and antibody fragments of the present invention are produced in transgenic animals. For example, transgenic sheep and cows may be engineered to produce the antibodies or antibody fragments in their milk (see, e.g., Pollock D P, et al., (1999) Transgenic milk as a method for the production of recombinant antibodies. J. Immunol. Methods 231:147-157, herein incorporated by reference). The antibodies and antibody fragments of the present invention may also be produced in plants (see, e.g., Larrick et al., (2001) Production of secretory IgA antibodies in plants. Biomol. Eng. 18:87-94, herein incorporated by reference). Additional methodologies and purification protocols are provided in Humphreys et al., (2001) Therapeutic antibody production technologies: molecules applications, expression and purification, Curr. Opin. Drug Discov. Devel. 4:172-185, herein incorporated by reference. In certain embodiments, the antibodies or antibody fragments of the present invention are produced by transgenic chickens (see, e.g., US Pat. Pub. Nos. 20020108132 and 20020028488, both of which are herein incorporated by reference).

III. Therapeutic Formulations and Uses

The CD20 binding molecules of the present invention (e.g. antibodies and antibody fragments) are useful for treating a subject with a disease. The CD20 binding molecules may also be used in diagnostic procedures (e.g. labeled CD20 binding molecules used, for tissue imaging). In preferred embodiments, the CD20 binding molecules are administered to a patient with B cell lymphoma, which is generally characterized by unabated B cell proliferation.

In some embodiments, the CD20 binding molecules are conjugated to various radiolabels for both diagnostic and therapeutic purposes. Radiolabels allow "imaging" of tumors and other tissue, as well helping to direct radiation treatment to tumors. Exemplary radiolabels include, but are not limited to, $^{131}I$, $^{125}I$, $^{123}I$, $^{99}Tc$, $^{67}Ga$, $^{111}In$, $^{188}Re$, $^{186}Re$, and preferably, $^{90}Y$.

In certain embodiments, the disease treated is Non-Hodgkin's lymphoma (NHL). In some embodiments, the disease is selected from relapsed Hodgkin's disease, resistant Hodgkin's disease high grade, low grade and intermediate grade non-Hodgkin's lymphomas (NHLs), B cell chronic lymphocytic leukemia (B-CLL), lymphoplasmacytoid lymphoma (LPL), mantle cell lymphoma (MCL), follicular lymphoma (FL), diffuse large cell lymphoma (DLCL), Burkitt's lymphoma (BL), AIDS-related lymphomas, monocytic B cell lymphoma, angioimmunoblastic lymphoadenopathy, small lymphocytic; follicular, diffuse large cell; diffuse small cleaved cell; large cell immunoblastic lymphoblastoma; small, non-cleaved; Burkitt's and non-Burkitt's; follicular, predominantly large cell; follicular, predominantly small cleaved cell; follicular, mixed small cleaved and large cell lymphomas, and systemic lupus erythematosus (SLE). In particular embodiments, the disease treated is Waldenstrom's Macroglobulinemia (WM) or Chronic Lymphocytic Leukemia (CLL).

In some embodiments, the CD20 binding molecules of the present invention are used for treatment of diseases wherein depletion of CD20+ cells is therapeutically beneficial, such as Waldenstrom's macroglobulinemia, multiple myeloma, plasma cell dyscrasias, chronic lymphocytic leukemia, treatment of transplant, hairy cell leukemia, ITP, Epstein Barr virus lymphomas after stem cell transplant, and Kidney transplant, see U.S. Pat. Pub. 20020128448, herein incorporated by reference. In other embodiments, the CD20 binding molecules of the present invention are used for the treatment of a disease selected from the group consisting of B cell lymphomas, leukemias, myelomas, autoimmune disease, transplant, graft-vs-host disease, infectious diseases involving B cells, lymphoproliferation diseases, and treatment of any disease or condition wherein suppression of B cell activity and/or humoral immunity is desirably suppressed. In certain embodiments, the CD20 binding molecules of the present invention are used for the treatment of a disease selected from the group consisting of B cell lymphomas, leukemia, myeloma, transplant, graft-vs-host disease, autoimmune disease, lymphoproliferation conditions, and other treatment diseases and conditions wherein the inhibition of humoral immunity, B cell function, and/or proliferation, is therapeutically beneficial. In further embodiments, the CD20 binding molecules of the present invention are used for the treatment of B-ALL, Hairy cell leukemia, Multiple myeloma, Richter Syndrome, Acquired Factor VIII inhibitors, Antiphospholipid syndrome, Autoimmune hemolytic anemia, Autoimmune thrombocytopenia, Bullous pemphigoid, Cold hemagglutinin disease, Evan's Syndrome, Goodpasture's syndrome, Idiopathic membranous nephropathy, Idiopathic thrombocytopenic purpura, IgM associated polyneuropathy, Kaposi sarcoma-associated herpesvirus (KSHV)-related multicentric Castleman's disease (MCD), Myasthenia gravis, Pemphigus vulgaris, Primary biliary cirrhosis, Pure red cell aplasia, Rheumatoid arthritis, Sjogren's Syndrome, Systemic immune complex vasculitis, Systemic lupus erythematosus, Type H mixed cryoglobulinemia, Wegener's granulomatosis, Allograft rejection, Post-transplant lymphoproliferative disease, or Purging of stem cells for bone marrow transplantation.

In preferred embodiments, the subject treat is not immunosuppressed (e.g. an SLE patient). While not limited to any mechanism, it is believe that the CD20 binding molecules of the present invention are less likely to illicit a HACA response than previously known anti-CD20 antibodies, especially in non-immunosuppressed patients. As such, non-immunosuppressed patients can be treated without the overriding concern for an adverse HACA reaction. Also, with the improved binding ability of the CD20 binding molecules of the present invention, lower doses may be administered to patients (further avoiding the risk of a HACA response), or higher doses may be administered without risking a life threatening HACA response. In other preferred embodiments, the subject has rheumatoid arthritis or other autoimmune disease (See, e.g., Edwards et al., *Rheumatology* (Oxford) 2001 February; 40(2):205-1 1, herein incorporated by reference).

The CD20 binding molecules of the present invention may also be administered in combination with other therapeutic moieties. For example, the CD20 binding molecules may be administered a part of a chemotherapeutic program (e.g. CHOP). The CD20 binding molecules may also be administered with cytokines, G-CSF, or IL-2 (See, U.S. Pat. No. 6,455,043, herein incorporated by reference).

The CD20 binding molecules of the present invention may be administered by any suitable means, including parenteral, non-parenteral, subcutaneous, topical, intraperitoneal, intrapulmonary, intranasal, and intralesional administration (e.g., for local immunosuppressive treatment). Parenteral infusions include, but are not limited to, intramuscular, intravenous, intra-arterial, intraperitoneal, or subcutaneous administration. In addition, CD20 binding molecules are suitably administered by pulse infusion, particularly with declining doses. Preferably, the dosing is given by injections, most preferably intravenous or subcutaneous injections, depending in part on whether the administration is brief or chronic.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is advantageous to formulate parenteral compositions in dosage unit form for ease of administration and uniformity of dosage. The dosages of the CD20 binding molecules of the present invention are generally dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody fragment (or other CD20 binding molecule of the invention) is 0.1-20 mg/kg, more preferably 1-10 mg/kg. In some embodiments, the dosage is from 50-600 mg/m$^2$ (e.g. 375 mg/m$^2$). It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the present invention.

The dosage administered will, of course, vary depending upon known factors such as the pharmacodynamic characteristics of the particular agent, its mode and route of administration, the age, health, and weight of the recipient, the nature and extent of symptoms, the kind of concurrent treatment, the frequency of treatment, and the effect desired. For example, a daily dosage of active ingredient can be about 0.01 to 100 milligrams per kilogram of body weight. Ordinarily 1.0 to 5, and preferably 1 to 10 milligrams per kilogram per day given in divided doses 1 to 6 times a day or in sustained release form, may be effective to obtain desired results.

The CD20 binding molecules of the invention can be incorporated into pharmaceutical compositions suitable for administration to a subject. For example, the pharmaceutical composition may comprise a CD20 binding molecule (e.g. an antibody or antibody fragment) and a pharmaceutically acceptable carrier. As used herein, "pharmaceutically acceptable carrier" includes solvents, dispersion media, coatings, antibacterial and antifungal agents, isotonic and absorption delaying agents, and the like that are physiologically compatible. Examples of pharmaceutically acceptable carriers include one or more of the following: water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the CD20 binding molecules.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies.

Therapeutic compositions typically are sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody fragment) in the required amount in an appropriate solvent with one or a combination of ingredients enumerated above, as required, followed by sterile filtration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see, e.g., Sustained and Controlled Release Drug Delivery Systems, J. R. Robinson. ed., Marcel Dekker, Inc., New York, 1978).

In certain embodiments, the CD20 binding molecules of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

The pharmaceutical compositions of the invention may include a "therapeutically effective amount" or a "prophylactically effective amount" of an antibody or antibody fragment of the invention. A "therapeutically effective amount" refers to an amount effective, at dosages and for periods of time necessary, to achieve the desired therapeutic result. A therapeutically effective amount of the antibody or antibody fragment may vary according to factors such as the disease state, age, sex, and weight of the individual, and the ability of the antibody or antibody fragment to elicit a desired response in the individual. A therapeutically effective amount is also one in which any toxic or detrimental effects of the antibody or antibody fragment are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

IV. Additional CD20 Binding Molecule Uses

CD20 binding molecules of the present invention, such as anti-CD20 peptides and/or antibodies are useful for immunoassays which detect or quantify CD20 in a sample or B cells bearing CD20. An immunoassay for CD20 typically comprises incubating a biological sample in the presence of a detectably labeled high affinity anti-CD20 peptide and/or antibody of the present invention capable of selectively binding to CD20, and detecting the labeled peptide or antibody which is bound in a sample. Various clinical assay procedures are well known in the art.

Thus, an anti-CD20 peptide or antibody, can be captured on nitrocellulose, or on any other solid support which is capable of immobilizing soluble proteins. A CD20-containing sample is then added to the support which is subsequently washed with suitable buffers to remove unbound proteins. A second, detectably labeled, CD20 specific peptide or antibody is added to the solid phase support that can then be washed with the buffer a second time to remove unbound detectably labeled peptide or antibody. The amount of bound label on the solid support can then be detected by known methods.

By "solid phase support" or "carrier" is intended any support capable of binding peptide, antigen or antibody. Well-known supports or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule retains its ability to bind to CD20. Thus, the support configuration can be spherical, as in a bead, or cylindrical, as in the inside surface of a test tube, or the external surface of a rod. Alternatively, the surface can be flat such as a sheet, culture dish, test strip, microtiter plates, etc. Preferred supports include polystyrene beads. Those skilled in the art will know many other suitable carriers for binding antibody, peptide or antigen, or can ascertain the same by routine experimentation. Well known methods can be used to determine the binding activity of a given lot of anti-CD20 peptide and/or antibody. Those skilled in the art can determine operative and optimal assay conditions by routine experimentation.

Detectably labeling a CD20 binding molecule, such as a CD20-specific peptide and/or antibody, can be accomplished by coupling to an enzyme for use in an enzyme immunoassay (EIA), or enzyme-linked immunosorbent assay (ELISA). The linked enzyme reacts with the exposed substrate to generate a chemical moiety which can be detected, for example, by spectrophotometric, fluorometric or by visual means. Enzymes which can be used to detectably label the CD20 binding molecules of the present invention include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the CD20 binding molecules, it is possible to detect CD20 through the use of a radioimmunoassay (RIA) (see, for example, Work, et al., (1978) Laboratory Techniques and Biochemistry in Molecular Biology, North Holland Publishing Company, N.Y.). The radioactive isotope can be detected by such means as the use of a gamma counter or a scintillation counter or by autoradiography.

It is also possible to label the CD20 binding molecules with a fluorescent compound. When the fluorescently labeled molecule is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The CD20 binding molecules can also be detectably labeled using fluorescence-emitting metals such as $^{125}$Eu, or others of the lanthanide series. These metals can be attached to the CD20 binding molecule using such metal chelating groups as diethylenetriaminepentaacetic acid (DTPA) or ethylenediamine-tetraacetic acid (EDTA).

The CD20 binding molecules also can be detectably labeled by coupling to a chemiluminescent compound. The presence of the chemiluminescently labeled molecule is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the CD20 binding molecules of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the CD20 binding molecules can be accomplished by a scintillation counter, for example, if the detectable label is a radioactive gamma emitter, or by a fluorometer, for example, if the label is a fluorescent material. In the case of an enzyme label, the detection can be accomplished by colorometric methods which employ a substrate for the enzyme. Detection can also be accomplished by visual comparison of the extent of enzymatic reaction of a substrate to similarly prepared standards.

In some embodiments of the present invention, the CD20 which is detected by the above assays can be present in a biological sample. Any sample containing CD20 can be used. Preferably, the sample is a biological fluid such as, for example, blood, serum, lymph, urine, cerebrospinal fluid, amniotic fluid, synovial fluid, a tissue extract or homogenate, and the like. However, the invention is not limited to assays using only these samples, as it is possible for one of ordinary skill in the art to determine suitable conditions which allow the use of other samples.

In situ detection can be accomplished by removing a histological specimen from a patient, and providing the combination of labeled CD20 binding molecules of the present invention to such a specimen. The CD20 binding molecule is preferably provided by applying or by overlaying the labeled CD20 binding molecule to a biological sample. Through the use of such a procedure, it is possible to determine not only the presence of CD20 but also the distribution of CD20 in the examined tissue. Using the present invention, those of ordinary skill will readily perceive that any of a wide variety of histological methods (such as staining procedures) can be modified in order to achieve such in situ detection.

The CD20 binding molecules of the present invention can be adapted for utilization in an immunometric assay, also known as a "two-site" or "sandwich" assay. In a typical immunometric assay, a quantity of unlabeled CD20 binding molecule (such as an anti-CD20 antibody) is bound to a solid support that is insoluble in the fluid being tested and a quantity of detectably labeled soluble antibody is added to permit detection and/or quantitation of the ternary complex formed between solid-phase antibody, antigen, and labeled antibody.

Typical, and preferred, immunometric assays include "forward" assays in which the CD20 binding molecule (e.g. antibody) bound to the solid phase is first contacted with the sample being tested to extract the CD20 from the sample by formation of a binary solid phase antibody-CD20 complex. After a suitable incubation period, the solid support is washed to remove the residue of the fluid sample, including unreacted CD20, if any, and then contacted with the solution containing a known quantity of labeled antibody (which functions as a "reporter molecule"). After a second incubation period to permit the labeled antibody to complex with the CD20 bound to the solid support through the unlabeled antibody, the solid support is washed a second time to remove the unreacted labeled antibody. This type of forward sandwich assay can be a simple "yes/no" assay to determine whether CD20 is present or can be made quantitative by comparing the measure of labeled antibody with that obtained for a standard sample containing known quantities of CD20.

Other types of "sandwich" assays, which can also be useful with CD20, are the so-called "simultaneous" and "reverse" assays. A simultaneous assay involves a single incubation step wherein the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay. In the "reverse" assay, stepwise addition first of a solution of labeled antibody to the fluid sample followed by the addition of unlabeled antibody bound to a solid support after a suitable incubation period, is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

In some embodiments, the CD20 binding molecules of this invention, attached to a solid support, can be used to remove CD20 (or B cells bearing CD20) from fluids or tissue or cell extracts. In a preferred embodiment, they are used to remove CD20 from blood or blood plasma products. In another preferred embodiment, the CD20 binding molecules are advantageously used in extracorporeal immunoadsorbent devices, which are known in the art (see, for example, Seminars in Hematology, 26 (2 Suppl. 1)(1989)). Patient blood or other body fluid is exposed to the attached CD20 binding molecule, resulting in partial or complete removal of circulating CD20 (free or in immune complexes), following which the fluid is returned to the body. This immunoadsorption can be implemented in a continuous flow arrangement, with or without interposing a cell centrifugation step. See, for example, Terman, et al., (1976) J. Immunol. 117:1971-1975.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: M (molar); mM (millimolar); nM (nanomolar); pM (picomolar); mg (milligrams); µg (micrograms); pg (picograms); ml (milliliters); µl (microliters); ° C. (degrees Celsius); OD (optical density); nm (nanometer); BSA (bovine serum albumin); and PBS (phosphate-buffered saline solution).

Example I

CD20 Binding Molecules

This example describes how certain, exemplary, CD20 binding molecules may be constructed. In particular, this example describes how eleven different CD20 binding molecules (AME 21E1 Hum, AME 6F1, AME 2C2, AME 1D10, AME 15, AME 18, AME 33, AME 5-3, AME 1C2, AME 4H5, and AME 5) may be constructed, and expressed, for example, as Fabs or full IgGs.

The light and heavy chain variable regions of the eleven different CD20 binding molecules may be constructed as follows. The collection of 6 CDRs for each of the CD20 binding molecules is shown in Table 3, with the sequence ID number for the amino acid sequence listed first and sequence ID number for the nucleic acid sequence listed second.

TABLE 3

Light and Heavy Chain CDRs in Exemplary CD20 Binding Molecules

| Anti-CD20 Molecule | CDRL1 SEQ ID NO: | CDRL2 SEQ ID NO: | CDRL3 SEQ ID NO: | CDRH1 SEQ ID NO: | CDRH2 SEQ ID NO: | CDRH3 SEQ ID NO: |
|---|---|---|---|---|---|---|
| AME 21E1 Hum | 1 and 2 | 7 and 8 | 19 and 20 | 23 and 24 | 27 and 28 | 49 and 50 |
| AME 6F1 | 1 and 2 | 7 and 8 | 19 and 20 | 23 and 24 | 27 and 28 | 51 and 52 |
| AME 2C2 | 1 and 2 | 7 and 8 | 19 and 20 | 23 and 24 | 33 and 34 | 53 and 54 |
| AME 1D10 | 5 and 6 | 7 and 8 | 19 and 20 | 23 and 24 | 33 and 34 | 53 and 54 |
| AME 15 | 5 and 6 | 7 and 8 | 19 and 20 | 23 and 24 | 35 and 36 | 53 and 54 |
| AME 18 | 5 and 6 | 13 and 14 | 19 and 20 | 25 and 26 | 37 and 38 | 55 and 56 |
| AME 33 | 5 and 6 | 13 and 14 | 19 and 20 | 25 and 26 | 39 and 40 | 57 and 58 |
| AME 5-3 | 1 and 2 | 7 and 8 | 17 and 18 | 23 and 24 | 27 and 28 | 43 and 44 |
| AME 1C2 | 3 and 4 | 9 and 10 | 17 and 18 | 23 and 24 | 29 and 30 | 45 and 46 |
| AME 4H5 | 3 and 4 | 7 and 8 | 17 and 18 | 23 and 24 | 31 and 32 | 47 and 48 |
| AME 5 | 3 and 4 | 11 and 12 | 21 and 22 | 23 and 24 | 31 and 32 | 45 and 46 |

The CDRs in Table 3 may be combined with any framework, such as a human germline framework, in order to generate variable regions (which may, for example, be expressed as Fvs). For example, in order to generate the variable regions for the eleven anti-CD20 molecules named in this example, the CDRs in table 3 are combined with human germline frameworks, as shown in Table 4.

TABLE 4

Human Germline Frameworks Used to Generate Named CD20 Binding Molecules

| Anti-CD20 Molecule | VL Framework | VH Framework |
|---|---|---|
| AME 5-3 | VkI (DPK4) (A20) | VHI DP7/21-2 |
| AME 1C2 | VkI (DPK4) (A20) | VHI DP7/21-2 |
| AME 4H5 | VkI (DPK4) (A20) | VHI DP7/21-2 |
| AME 5 | VkI (DPK4) (A20) | VHI DP7/21-2 |
| AME 21E1 Hum | VkIII (A27) (DPK22) | VH5-51 (DP-73) |
| AME 6F1 | VkIII (A27) (DPK22) | VH5-51 (DP-73) |
| AME 2C2 | VkIII (A27) (DPK22) | VH5-51 (DP-73) |
| AME 1D10 | VkIII (A27) (DPK22) | VH5-51 (DP-73) |
| AME 15 | VkIII (A27) (DPK22) | VH5-51 (DP-73) |
| AME 18 | VkIII (A27) (DPK22) | VH5-51 (DP-73) |
| AME 33 | VkIII (A27) (DPK22) | VH5-51 (DP-73) |

The sequences for the full light and heavy chain variable regions of two of the eleven CD20 binding molecules is provided in FIGS. 2-5. In particular, FIGS. 2 and 3 show the amino acid and nucleic acid sequences for the light and heavy chain variable regions of AME 33 (which, together, provides the full Fv sequence for AME 33). FIGS. 4 and 5 show the amino acid and nucleic acid sequences for the light and heavy chain variable regions of AME 5.

The light and heavy chain variable regions for the eleven CD20 binding molecules discussed in this example may be combined with light and heavy chain constant regions and expressed as Fabs or full antibodies (e.g. IgG). These sequences are preferably linked to a leader sequence (e.g. a leader sequence at the beginning of the light chain sequence). One example of leader sequence that may be employed is METPAQLLFLLLLWLPDTTG (SEQ ID NO:105). Other leader sequences may be employed. Also, any human constant region allotype chain may be employed. For example, FIGS. 6 and 7 show the complete light and heavy chains for AME 33, which include the light and heavy chain constant regions. These figures may also be the source of the constant regions used to make the Fab and IgGs of the other CD20 binding molecules named in this example. It is noted that the constant regions are underlined in FIGS. 6A and 7A. Also, the anti-CD20 molecules in this example may alternatively employ the heavy chain constant regions shown in FIGS. 6 and 7, except with an amino acid substitution in the Fc region. In particular, the heavy chain constant region shown in FIG. 7 may contain a D280H mutation or a K290S mutation (FIG. 7A shows positions 280 and 290 in bold, without the mutations). FIG. 7B shows a bold and underlined "GAC." This "GAC" may be changed to "CAT" in order to encode the D280H mutation.

In order to express the anti-CD20 binding molecules in this example (as Fabs or IgGs), procedures known in the art may be used. For example, the eleven CD20 binding molecules in this example can be expressed, as Fabs or IgG's, in mammalian expression systems (or bacterial, fungal and plant expression systems) using either a single vector or double vector system. In a single vector system both heavy and light chains are manufactured or cloned within an expression cassette, which contains all required regulatory elements for expression. A double vector system simply has these two expression cassettes in separate plasmids. Either the single, or combined plasmids in the double vector system, may be transfected into a host cell line such as Chinese Hamster Ovary (CHO) cells or the retinal cell line PerC6, selected for, expanded and cultured to express the Fab or IgG proteins as is known in the art (see Antibody Expression and Engineering: Developed from a Symposium Sponsored by the Division of Biochemical Technology at the 207th National Meeting of the American Chemical Society, San Diego [ACS Symposium Series, 604]).

Fabs may also be expressed in a bacterial expression system, as this is less time consuming and less expensive than mammalian systems. Here Fabs can be inserted and expressed within a M13 viral expression system. Bacterial expressed Fabs are secreted and also accumulate within the periplasmic space between the bacterial cell wall and its cell membrane. The Fab can be released from this periplasmic space by a number of techniques including hypotonic shock and freeze thaw procedures common in the art. Fab's can also be generated from intact IgG by proteolytic cleavage using a protease such as papain. The Fab portion of the cleavage product can then be purified away from the Fc portion of the cleavage product. Fabs and IgG's can be purified with any variety of chromatographic and specific adsorption techniques that are also known in the art (see *Antibodies: A Laboratory Manual*, by Ed Harlow (Editor), David Lane (Editor), Cold Spring Harbor Press). For example IgG's can be easily purified from cellular supernatants by specific binding using rProtein A affinity chromatography followed by Mono S cation exchange chromatography.

Example 2

Fixed Ramos Cell ELISA

This example describes a fixed Ramos cell ELISA binding assay with CD20 binding molecules. In particular, this example assayed AME 4H5, AME 15, AME 18, AME 33 and AME 1D10 expressed as Fab and IgG to determine overall binding, off-rate, and on-rate. This example also tested in house C2B8 fabs and full antibody, as well as commercial RITUXAN (Oncology Supply Co.) in the same assay for comparison purposes. The C2B8 antibody is deposited with the ATCC as deposit number 69119.

Ramos cells (ATCC) were grown in RPMI 1640 containing 10% heat inactivated Fetal Bovine Serum. Fifty microliters of Ramos cells ($2\text{-}4\times10^6$/ml), were pipetted into each well of a 96 well Poly-D-Lysine coated plate (BIOCAT Becton Dickinson Labware) and incubated at 37° C., 5% $CO_2$ for 18 hours. Media was gently aspirated and 100 ml of aqueous buffered zinc formalin (Anatech, Ltd.) was added to each well for 15 minutes at room temperature. Z-fix was removed and the plate was washed with phosphate-buffered saline (PBS) containing 0.05% Tween 20. The plate was blocked for 1 hour with 1% bovine serum albumin (BSA) in PBS. Dilutions of Fab or IgG were incubated with the fixed and blocked Ramos cells for 1 hour at room temperature. The plate was washed 3× with PBS 0.05% Tween 20, and 50 ml of anti-His6 Peroxidase Mouse Monoclonal Antibody (Roche Diagnostics Corporation) at a 1:500 dilution were added to the wells and incubated 1 hour at room temperature. The plate was washed as above and developed with tetramethyl benzidine, and the reaction was stopped with 5N $H_2SO_4$. The plate absorbance was read at OD 450 nm. Dilutions of Fab and conjugate were in 1% BSA/PBS.

IgG assays were performed similarly except IgG bound was detected with goat anti-human IgG-HRP. To compare antibody off-rate, after incubation with Fab or IgG the plates were incubated over night in PBS/BSA, before proceeding with the second antibody step. To compare antibody on-rate, incubation steps for Fab/IgG binding and with the second antibody were both of 5 minutes duration.

The results from this example are presented in FIGS. 8 and 9. As shown in these figures, overall binding of Fabs AME 4H5, 15, 18, 33 and 1D10 are more effective than C2B8 Fab. The dose-response curve for the AME antibodies is shifted to the left relative to the C2B8 antibody and commercial RITUXAN, and the maximum OD attained is approximately 1.5 times that seen with the C2B8 antibody. In regard to off-rate, Fabs of AME 4H5, 15, 18, 33 and 1D10 show a dramatically decreased off-rate relative to C2B8 Fab (FIG. 8B). The off-rate for AME antibodies expressed as whole IgGs is similar to that of the C2B8 antibody and commercial RITUXAN (FIG. 9A). In regard to on-rate, Fabs of AME 4H5, 15, 18, 33 and 1D10 show an on-rate similar to that of the C2B8 Fab, with increased overall binding (maximum OD attained) (FIG. 8C). The dose-response for AME antibodies expressed as whole IgGs is shifted to the left of that of the full C2B8 antibody (FIG. 9B).

Example 3

Immunofluorescent Live B Lymphoma Binding Assays

This example describes immunofluorescent live B lymphoma binding assays. In particular, Fabs of AME 33, AME 5 and C2B8 were assayed as described below.

Fab Staining of PBMC's for CD20 FACS Analysis

Peripheral blood mononuclear cells (PBMC) were isolated from normal human blood by flotation on Ficol-Hypaque (Sigma-1077). Cells were counted and resuspended in PBS+ 1% BSA to give 2-5×10$^6$ cells/ml. One hundred microliters of diluted cells were dispensed into polystyrene tubes (Falcon #2058) and anti-CD20 Fab antibodies diluted in PBS+1% BSA were added. Tubes were incubated 1 hour at room temperature. Four milliliters of PBS+1% BSA were added to each tube and the tubes were centrifuged at 300×G for 10 minutes. The supernatant was removed and the cells resuspended in 100 µl PBS+1% BSA. Anti-Penta-His AlexaFluor 488 conjugate (Qiagen #35310), 2 µl per tube, was added, the tubes were mixed and incubated for 1 hour in the dark at room temperature. Samples were washed as previously described. The supernatant was removed and the cells resuspended in PBS+1% BSA+2 µg/ml Propidium iodide. Fluorescence was analyzed on a Becton Dickinson FACScan or FACSort flow cytometer and data analyzed using Cell Quest (Becton Dickinson) or WinMDI software.

The results are presented in FIG. 10. Results for Daudi cells are shown in FIG. 10A, results for Wil2-S cells are shown in FIG. 10B, and results for Ramos cells are shown in FIG. 10C. As shown in this figure, Fabs of AME 5 and 33 are more effective in binding to live B lymphoma cell lines than C2B8. It is noted that the dose response curve for AME 5 and AME 33 is shifted to the left relative to C2B8.

Example 4

IgG Binding Measured by KinExA

This example describes assays for measuring Kd, Kon, and Koff of various CD20 IgGs. In particular, this assay tested AME 33, AME 5, AME 6F1, and the C2B8 antibody for their binding to SKW 6.4 B lymphoma cells and determined Kd, Kon, and Koff for each of these molecules with the aid of KinExa equilibrium software. In addition, AME 33 and C2B8 were tested for binding to primary human peripheral blood B cells.

Kd Measurement:

SKW 6.4 cells were grown in DMEM media supplemented with 10% FCS and harvested at 5–10×10$^5$ cells per ml. The cells were washed with 5 volumes of PBS and re-suspended in PBS with 1% BSA at approx. 1×10$^8$ cells per ml. For human peripheral blood B cells, fresh CD19 positively sorted B cells were obtained from Allcells. These cells were washed two times in PBS with 1% BSA and resuspended at a concentration of 8×10$^7$/ml.

Twelve, 3 fold serial dilutions were then made and 100 µl of each dilution placed in a 96 well plate. To each dilution 100 ml of antibody at 100 ng/ml was added and the plate incubated at 37° C., 5% CO$_2$ for 4 hours. Each sample was then filtered with a 96 well 1 micron filter (Millipore) to remove the cells and bound antibody. Free antibody in solution was then quantified using an ELISA. Briefly, free IgG was captured in a 96 well plate coated with 1 mg/ml of anti-human kappa antibody (Southern Biotechnology) and detected using an anti-human Fc antibody coupled with HRP (Southern Biotechnology). The plate was developed using Fast TMB substrate (Pierce) and read at 450 nm.

The Kd of the antibody was then determined using the KinExA equilibrium software for an unknown antigen concentration. The OD450 value for each serial dilution was fitted with an estimated antigen concentration and the actual antibody concentration. The Kd and actual antigen concentration were then calculated. The results for the SKW 6.4 cell assays are shown in Table 5. These results show that AME 33 and AME 5 have a Kd that is 10-fold enhanced compared to the C2B8 antibody. The results for the primary human peripheral blood B cells show a Kd for AME 33 of 113 pM and a Kd for C2B8 of 1500 pM. Again, AME 33 is shown to have a Kd greater than 10-fold (almost fifteen fold) that of the C2B8 antibody.

TABLE 5

|  | AME 33 | AME 5 | AME 6F1 | C2B8 |
| --- | --- | --- | --- | --- |
| Kd; pM | 97 | 145 | 2500 | 2097 |
| Kon; ×10$^5$ M$^{-1}$, s$^{-1}$ | 7.8 | 5.8 | 1.0 | 4.7 |
| Koff; ×10$^{-5}$ s$^{-1}$ | 7.7 | 7.9 | 25.0 | 104.5 |

Kinetic Measurements:

SKW 6.4 cells were grown in DMEM media supplemented with 10% FCS and harvested at 5–10×10$^5$ cells per ml. The cells were washed with 5 volumes of PBS and re-suspended in PBS with 1% BSA at approx. 1×10$^7$ cells per ml and kept in a water bath at 37° C. An equal volume of antibody at 100 ng/ml in PBS with 1% BSA at 37° C. was then added to the cells and the timing for the experiment started. At time intervals from 60 seconds to 10800 seconds a sample of the antibody cell solution was sampled and filtered to remove cells and bound antibody. Free antibody remaining at each time point was then quantified using the ELISA described above.

The kinetics for the antibody cell reaction was calculated using the direct kinetics KinExA software. The OD450 value for each time point was fitted using the previously calculated Kd and antigen concentration and the Kon and Koff for the reaction calculated. The results are shown in Table 5.

Example 5

ADCC Assays with CD20 Binding Molecules

In this example, AME 5, AME 33, and AME 6F1 IgGs, as well as the C2B8 antibody, were tested for their ability to mediate antibody-dependent cell mediated cytotoxicity (ADCC) using human peripheral blood mononuclear cells as effectors and B lymphoma cell lines as targets. These assays were performed as described below.

PBMC (Peripheral Blood Mononuclear Cell) Isolation

Peripheral blood from healthy donors was diluted 1:2 with phosphate buffered saline (PBS), pH 7.0. Twelve mL of Histopaque-1077 (Sigma Cat. No. 1077-1) was carefully layered underneath the diluted sample followed by centrifugation in a Sorvall RT6000B centrifuge with swinging bucket rotor at 1000 rpm for 10 minutes with the brake turned off. The PBMC-containing interphase was collected and washed 3 times with Hanks' Balanced Salt Solution (Gibco). The washed cell pellet was suspended in 20 mL RPMI 1640 Media (ATCC) containing 10% Fetal Bovine Serum (FBS) (Omega Scientific). The resuspended PBMCs were split into two T-175 culture flasks and 30 mL of RPMI/10% FBS was added to each. Flasks were incubated overnight in a 37° C./5% CO$_2$ incubator. The following day the nonadherent PBMCs were collected, centrifuged as above, resuspended in RPMI containing 1% FBS and counted using a hemocytometer.

Target Cell Lines

B lymphoma cell lines were obtained from ATCC and grown as recommended. The day before the experiment the cells were split 1:2. The next day the concentration was adjusted to 0.5 to 1×10⁶ cells/mL and 50 μL (25,000 to 50,000 cells/well) aliquots added to a Becton Dickinson 96-well U-bottom tissue culture plate.

IgG Titrations

IgG dilutions were prepared by diluting the samples in RPMI containing 1% FBS. Fifty microliter aliquots of IgG were added to the target cells in a 96-well microtiter plate and mixed by gentle pipetting. The IgGs were incubated with the target cells for 15 minutes at 37° C./5% $CO_2$ prior to adding the effector cells.

Effector Cells

One hundred microliters of the resuspended PBMCs were added to each well of the target cell/IgG plate. The concentration of the PBMCs was adjusted so that the effector:target ratio was in the range of 10-20:1. The plates were incubated at 37° C./5% $CO_2$ for 3-4 hours.

LDH-Release Detection

Following incubation, the plate was centrifuged at 1-2000 rpm for 5-10 min. Fifty μL of the supernatant was carefully removed avoiding pelleted cells. This supernatant was added directly to a Dynex Immulon 2HB flat bottom plate containing 50 pL of PBS per well. To this plate was added 100 μl of LDH detection reagent (Roche). The plate was then incubated for approximately 15-30 minutes and OD read at 490 nm using a Molecular Devices Vmax Kinetic Microplate Reader.

Data Analysis

Figure 11:
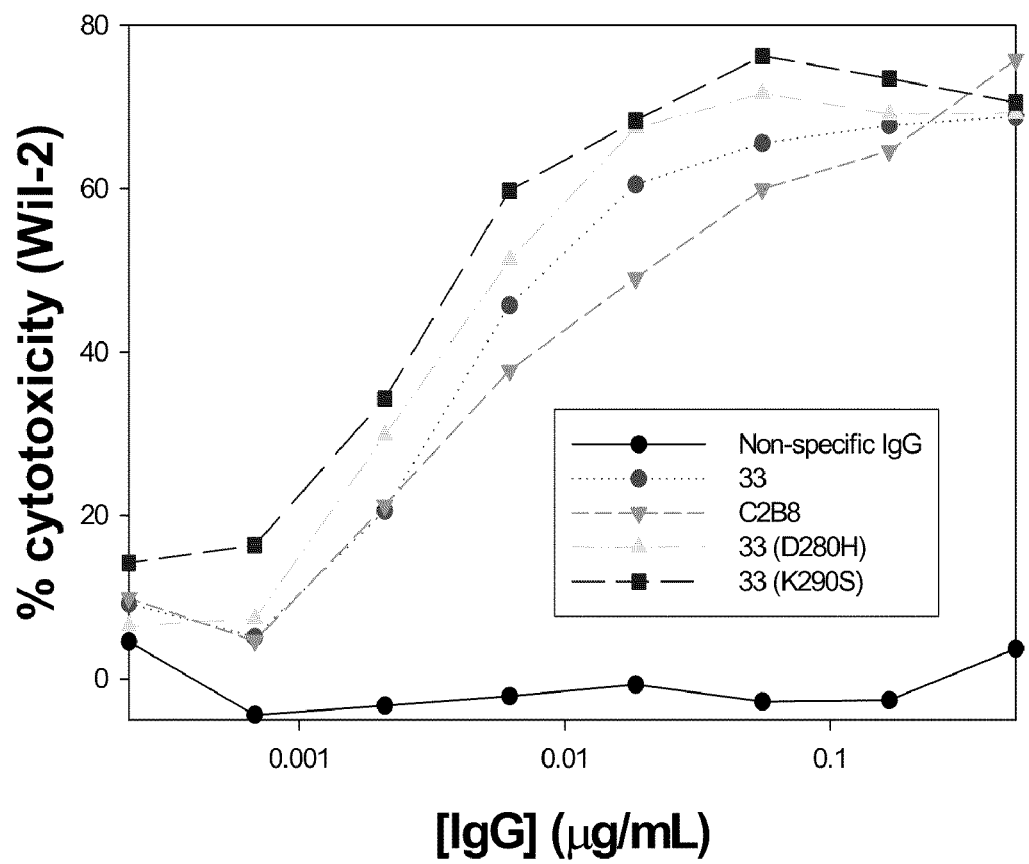
FIG. 11 shows the results of the ADCC assay described in Example 5.

Data were plotted as log IgG concentration vs. A490 (See FIG. 11). A490 was converted into % cytotoxicity using the following equation: % cytotoxicity=(experimental A490–basal A490)/(maximal A490–basal A490)×100, with maximal A490 determined by adding 2% Triton X-100 to the target cells and basal-release measured for a mixture of effector and target cells in the absence of sensitizing IgG. Based on the data shown in FIG. 11, it was shown that the EC50 of AME 33 with the Fc mutations D280H and K290S were consistently 1.5-2.0 times lower than C2B8. This data is also presented in Table 6 below.

TABLE 6

| Estimated EC50s, ug/ml (Wil-2 cells as target) | |
|---|---|
| C2B8 | 0.0042 +/− .0008 |
| AME 33 | 0.0063 +/− .0031 |
| AME 33 D280H | 0.0031 +/− .0009 |
| AME 33 K290S | 0.0021 +/− .0005 |

Example 6

Glycoengineering of CD20 Binding Molecules

This example describes glycoengineering methods that were applied to certain CD20 binding molecules. In particular, AME 1C2 IgG bearing wild-type or mutant (D280H or K290S) Fc regions was coexpressed in CHO cells together with the enzyme (β(1-4)-N-acetylglucosaminyltransferase III to increase expression of bisected oligosaccharides in the Fc region. The combination of glycoengineering and mutant Fc region decreased the EC50 of 1C2 in ADCC assays relative to unmodified 1C2 or the commercial RITUXAN antibody. The method was performed as described below.

The (β(1-4)-N-acetylglucosaminyltransferase III gene was PCR amplified from rat kidney cDNA (Clontech, Palo Alto, Calif.). The PCR primers introduced a NheI site at the 5'-end of the gene and a EcoRI site at the 3'-end of the gene (forward primer was 5'-GGCGGCTAGCATGAGACGCTA-CAAGCTTTTTCTCATGTTCTG-3', SEQ ID NO:103, and the reverse primer was 5'-GGCGGAATTCCTAGCCCTC-CGTTGTATCCAACTTGC-3', SEQ ID NO:104). Following restriction digestion and purification of the PCR product it was ligated into similarly cleaved pcDNA3.1 NEO (Invitrogen, Carlsbad, Calif.). The ligated plasmid DNA was used to transform E. coli by electroporation. Ampicillin resistant E. coli colonies were screened for the presence of the rat (β(1-4)-N-acetylglucosaminyltransferase III gene using colony PCR. Plasmid DNA was isolated from positive clones and sequenced. Sequence confirmed plasmid DNA was linearized with BspHI and about 10 micrograms of the linear DNA used to transfect CHO K1 cells using Lipofectamine 2000 (Invitrogen, Carlsbad, Calif.) following the manufacturer's protocol. Following G418 selection, isolated resistant colonies were expanded in tissue culture. mRNA was isolated and screened for the qualitative production of the rat β(1-4)-N-acetylglucosaminyltransferase III messenger RNA. Each of these cell lines yielded a PCR product of the anticipated size whereas untransfected CHOK1 cells did not. DNA encoding anti-CD20 IgG was used to transfect stable cell lines. Approximately three days following transfection, cell culture supernatants were collected and the IgG affinity purified using protein A chromatography. Following elution of the IgGs from the protein A column the samples were dialyzed and the protein concentration quantitated by measuring its absorbance at 280 nm.

Figure 12:
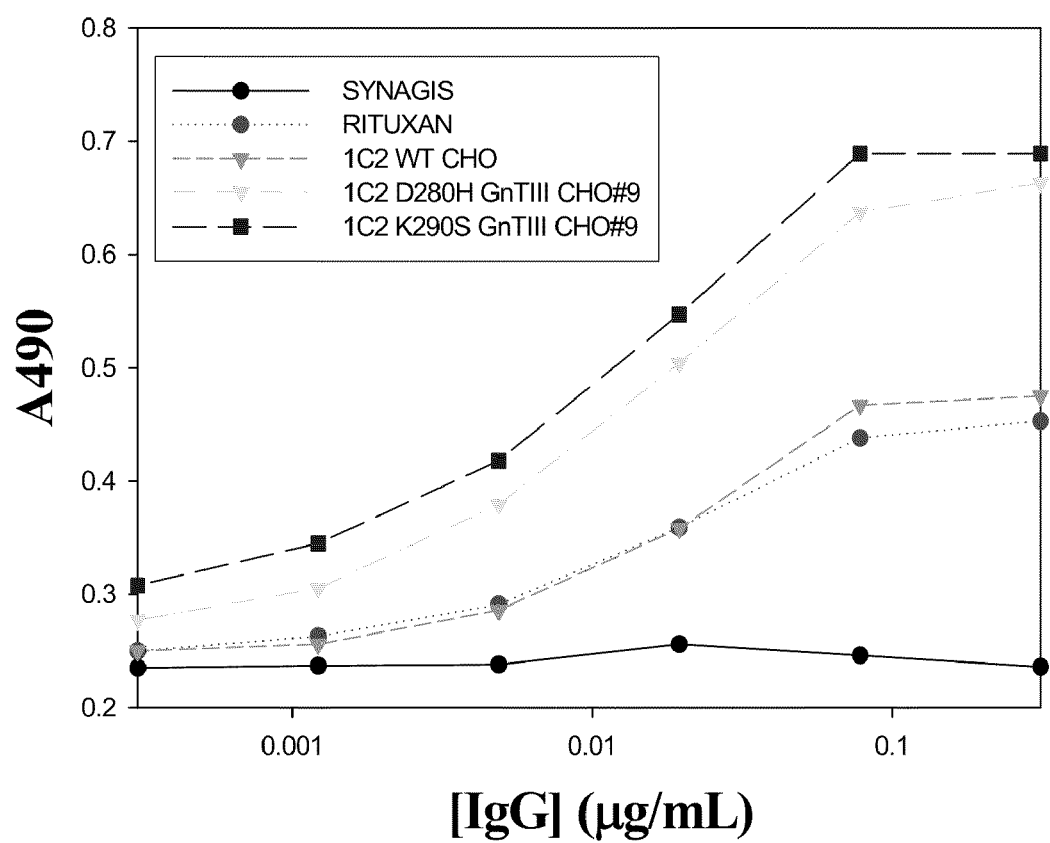
FIG. 12 shows the ADCC activity of the glycoengineered CD20 binding molecule described in Example 6.

The IgG samples expressed from the different CHOK1 cell lines were tested for the ability to elicit antibody dependent cell-mediated cytotoxicity (ADCC) using methods described in Example 5. Peripheral blood lymphocytes, isolated from fresh human blood were used as the effector cells and WIL.2s B cells were used as the target cells in these experiments. The amount of target cell lysis was measured using a standard lactate dehydrogenase release assay. The IgG expressed from the engineered CHOK1 cell lines were compared directly with IgG expressed from non-engineered CHOK1 cell lines and commercial RITUXAN antibody for the ability to elicit ADCC. In addition the presence of a bisecting N-acetylglucosamine sugar moiety was confirmed by direct glycosylation analysis. The results of the ADCC assays for AME 1C2 are shown in FIG. 12.

Example 7

In Vitro Apoptosis Assays

This example describes certain in vitro apoptosis assays conducted with various CD20 binding molecules. In particular, AME 5, AME 33 and AME 6F1 (all as full antibodies), as well as the C2B8 antibody, were tested for their ability to induce apoptosis of the Ramos B lymphoma cell line following cross-linking with anti-human IgG. These assays were performed as described below.

Annexin V-FITC Staining

The Ramos B lymphoma cell line (ATCC) was split 1:2 24 hours before use. On the day of assay, Ramos cells were centrifuged (1,000 rpm for 5 min.), washed with PBS, and resuspended in RPMI plus 10% heat-inactivated FBS (media) at a cell density of 5×10⁵ cells/ml. One million cells were added per well of a 6 well tissue culture plate. Primary antibody was added to the cells at the indicated concentrations, plates were gently shaken for 15 minutes and then returned to 37° C. for an additional 45 minutes. Two ml of pre-warmed goat anti-human IgG (10 μg/ml) or medium were added to specified wells and the plates were incubated at 37° C. for 6 hours.

Cells were harvested by centrifugation (1,000 rpm for 5 min.) and resuspended in 100 μl cold 1× binding buffer (diluted in water from 10× stock) and 10 μl Annexin V-FITC (Southern Biotech). Samples were transferred to polystyrene round-bottom tubes (Falcon 2058) and incubated in the dark for 15 minutes at room temperature. Binding buffer containing propidium iodide, 2 μg/ml, was added and samples were analyzed on a Becton Dickinson Facscan flow cytometer using CellQuest or WinMDI software for data analysis. Cell death (% apoptotic plus necrotic cells) was determined by measuring the percentage of cells staining with Annexin V. The results of this assay showed that AME 5, 33 and 6F1 induced cell death at levels similar to that observed with C2B8 antibody treatment.

Example 8

Complement Mediated Cytotoxicity Assays

This example describes how the C2B8 antibody, Synagis (control) and AME antibodies 6F1, 2C2, 1D10, 15, 18, and 33 were tested for their ability to mediate complement-dependent cytotoxicity using human complement and the Wil-2 B lymphoma cell line as target.

Wil2-S B-lymphoma cells (ATCC) were resuspended at $5 \times 10^5$/ml in RPMI+10% heat-inactivated FBS. Fifty microliters of Wil2-S cell suspension, 50 μl IgG (ranging in concentration from 1 ng/ml to 75 μg/ml), and 50 μA diluted [1:5] human complement were mixed in a 96 well plate (Costar 3917). Antibody and complement were diluted in RPMI+ 10% FBS. Antibody and complement are diluted in RPMI+ 10% FBS. The cells were incubated for 90 minutes at 37° in 5% $CO_2$. Alamar Blue, 15 μl per well, was added and the plate incubated overnight at 37° in 5% $CO_2$. Fluorescence (reflecting the number of live cells) was recorded using 560 nm excitation and detecting emission at 590 nm. The results of these assays show that the EC50s of all AME antibodies tested was similar to that of the C2B8 antibody.

Example 9

In Vivo CD20 Binding Molecule Administration

This example describes assays that were used to test a number of CD20 binding molecules in vivo.

Antibodies AME 45H, 1C2, 5-3, as well as the C2B8 antibody, were assayed in mice as follows. Male 6-8 week-old C.B.17-SCID mice (Taconic) were injected s.c. in the right and left flanks with $5 \times 10^6$ Raji cells (ATCC). Antibodies were injected intraperitoneally at 0.01 mg/kg, 0.05 mg/kg, 0.1 mg/kg and 0.5 mg/kg approximately 2-3 hrs later (Day 0). Tumor length, width and height were measured by caliper every Monday, Wednesday and Friday and tumor volume calculated. $EC_{50}$ values were determined from the dose-response curves. The EC50's of AME 4H5, 1C2, and 5-3 were not consistently different than the EC50 for the C2B8 antibody.

Figure 13:
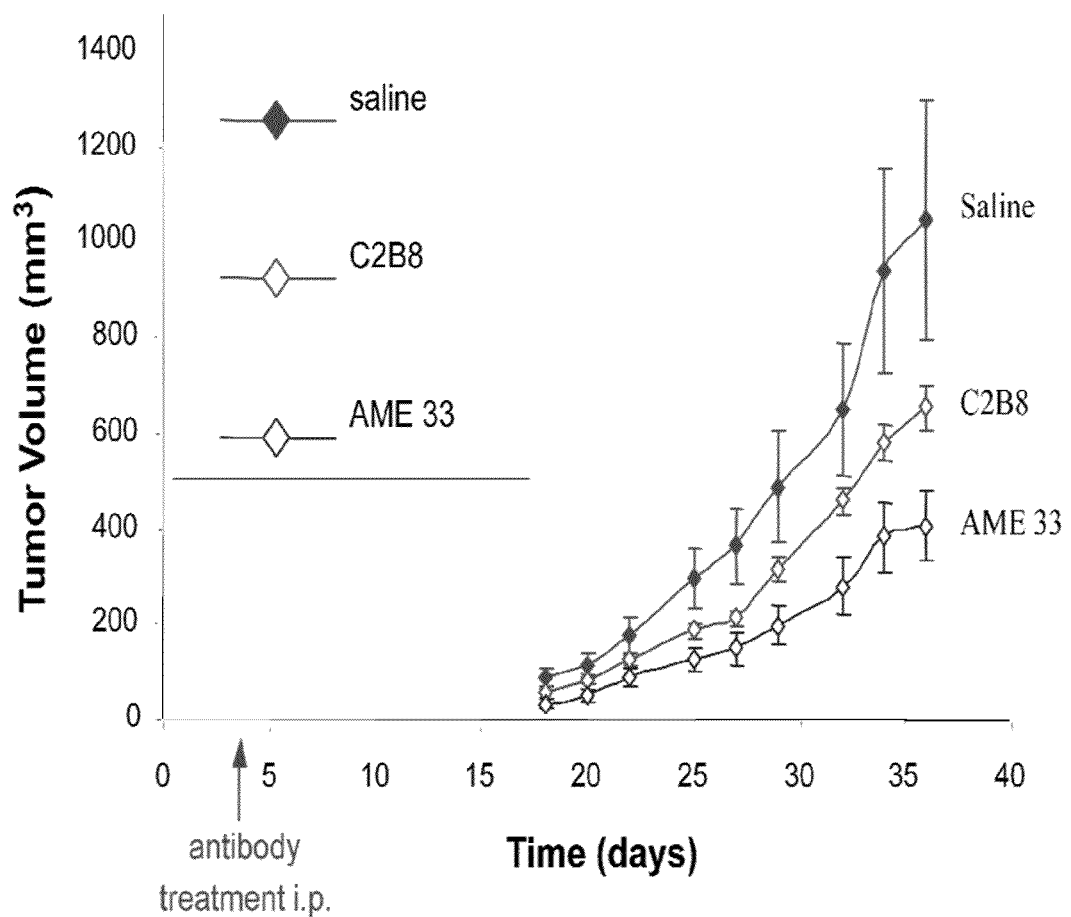
FIG. 13 shows the results of an in vivo tumor inhibition assay described in Example 9 involving the AME 33 antibody and the C2B8 antibody.

Antibody AME 33 and the C2B8 antibody were also assayed in mice that had been injected with $5 \times 10^6$ Raji cells. Mice were treated on day three with 0.5 mg/kg AME 33 or C2B8. Control mice received saline. The results (shown in FIG. 13) show that AME 33 and C2B8 inhibited the growth of Raji tumors in a similar manner, with AME 33 allowing less tumor growth over time compared to C2B8.

Example 10

Use of CD20 Binding Molecules to Treat Disease in Humans

This example describes the use of CD20 binding molecules for the therapeutic and prophylactic treatment of certain diseases in a human patient including, but not limited to, a disorder selected from Non-Hodgkin's Lymphoma (NHL) and systemic lupus erythematosus (SLE).

For example, a patient with one of the diseases listed above may be administered a CD20 binding molecule such as AME 21E1 Hum, AME 6F1, AME 2C2, AME 1D10, AME 15, AME 18, AME 33, AME 5-3, AME 1C2, AME 4H5, or AME 5, intravenously at 0.4 to 20.0 mg/kg body weight. A typical dosage schedule, may be, for example, 375 mg/m² of the antibody administered as a slow IV infusion once weekly for 4 or 8 doses. Additional dosage regimes are provided in U.S. Pat. No. 6,399,061 to Anderson, herein incorporated by reference in its entirety for all purposes. The antibody, or Fab fragment, may also be radiolabeled (e.g. with Yttrium-[90]) for therapy and/or in vivo imaging procedures (See, U.S. Pat. No. 6,399,061). Response to therapy may be monitored to determine the need for increased or reduced dosage and the need for repeat treatment. Additional guidance on response to therapy and dosage schedules is found in U.S. Pat. No. 6,399,061.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, medicine, and molecular biology or related fields are intended to be within the scope of the following claims.

We claim:

1. A composition comprising a CD20 binding molecule, wherein the CD20 binding molecule comprises a light chain variable region and a heavy chain variable region, wherein:
   the light chain variable region comprises:
      a CDRL1 amino acid sequence of SEQ ID NO:5;
      a CDRL2 amino acid sequence of SEQ ID NO:13;
      a CDRL3 amino acid sequence SEQ ID NO:19, and
   the heavy chain variable region comprises:
      a CDRH1 amino acid sequence of SEQ ID NO:25;
      a CDRH2 amino acid sequence of SEQ ID NO:39; and
      a CDRH3 amino acid sequence of SEQ ID NO:57.

2. A method of treating B cell lymphoma comprising administering to a subject a composition comprising a CD20 binding molecule, wherein the CD20 binding molecule comprises a light chain variable region and a heavy chain variable region, wherein:
   the light chain variable region comprises:
      a CDRL1 amino acid sequence of SEQ ID NO:5;
      a CDRL2 amino acid sequence of SEQ ID NO:13; and
      a CDRL3 amino acid sequence of SEQ ID NO:19, and
   the heavy chain variable region comprises:
      a CDRH1 amino acid sequence of SEQ ID NO:25;
      a CDRH2 amino acid sequence of SEQ ID NO:39; and
      a CDRH3 amino acid sequence of SEQ ID NO:57.

3. The method of claim 2, wherein the CD20 binding molecule comprises the AME 33 Fab.

4. The method of claim 2, wherein the CD20 binding molecule has a binding affinity ($K_d$) for human CD20 of $5.0 \times 10^{-10}$ M or less, and a dissociation rate (koff) for human CD20 of $5.0 \times 10^{-4}$ s$^{-1}$ or less.

5. The method of claim 4, wherein the CD20 binding molecule has a binding affinity ($K_d$) for human CD20 of $1.5 \times 10^{-10}$ M or less.

6. The method of claim 4, wherein the CD20 binding molecule has a dissociation rate ($k_{off}$) for human CD20 of $2.5 \times 10^{-4}$ s$^{-1}$ or less.

7. The method of claim 4, wherein the CD20 binding molecule has an association rate ($k_{on}$) for human CD20 of $5.0 \times 10^{-5}$ M$^{-1}$ s$^{-1}$ or greater.

8. The method of claim 2, wherein the B cell lymphoma is Non-Hodgkin's lymphoma.

9. The method of claim 8, wherein the Non-Hodgkin's lymphoma is Waldenstrom's macroglobulinemia.

10. The composition of claim 1, wherein the light chain variable region comprises an amino acid sequence of SEQ ID NO:59 and the heavy chain variable region comprises an amino acid sequence of SEQ ID NO:61.

11. A composition comprising a CD20 binding molecule, wherein the CD20 binding molecule comprises a light chain amino acid sequence of SEQ ID NO:67 and a heavy chain amino acid sequence of SEQ ID NO:69.

* * * * *

SEQUENCE LISTING

```
<160> NUMBER OF SEQ ID NOS: 102

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(10)
```

<223> OTHER INFORMATION: CDRL1

<400> SEQUENCE: 1

Arg Ala Ser Ser Ser Val Ser Tyr Ile His
1               5                   10

<210> SEQ ID NO 2
<211> LENGTH: 30
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(30)
<223> OTHER INFORMATION: CDRL1

<400> SEQUENCE: 2
agggccagct caagtgtaag ttacatccac                                    30

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(10)
<223> OTHER INFORMATION: CDRL1

<400> SEQUENCE: 3

Arg Ala Ser Ser Ser Val His Tyr Ile His
1               5                   10

<210> SEQ ID NO 4
<211> LENGTH: 30
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(30)
<223> OTHER INFORMATION: CDRL1

<400> SEQUENCE: 4
agggccagct caagtgtaca ttacatccac                                    30

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(10)
<223> OTHER INFORMATION: CDRL1

<400> SEQUENCE: 5

Arg Ala Ser Ser Ser Val Pro Tyr Ile His
1               5                   10

<210> SEQ ID NO 6
<211> LENGTH: 30
<212> TYPE: DNA
<213> ORGANISM: Artificial Sequence
<220> FEATURE:
<223> OTHER INFORMATION: Synthetic Construct

```
<220> FEATURE:
<221> NAME/KEY: misc_feature
<222> LOCATION: (1)..(30)
<223> OTHER INFORMATION: CDRL1

<400> SEQUENCE: 6
agggccagct caagtgtacc gtacatccac                                           30

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: CDRL2

<400> SEQUENCE: 7

Ala Thr Ser Asn Leu Ala Ser
1               5

<210> SEQ ID NO 8
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(21)
<223> OTHER INFORMATION: CDRL2

<400> SEQUENCE: 8
gccacatcca acctggcttc t                                                    21

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: CDRL2

<400> SEQUENCE: 9

Ala Thr Thr Asn Leu Ala Thr
1               5

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(21)
<223> OTHER INFORMATION: CDRL2

<400> SEQUENCE: 10
gccacaacca acctggctac g                                                    21

<210> SEQ ID NO 11
<211> LENGTH: 7
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: CDRL2

<400> SEQUENCE: 11

Ala Thr Ser Gly Leu Ala Ser
1               5

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(21)
<223> OTHER INFORMATION: CDRL2

<400> SEQUENCE: 12
gccacatccg gcctggcttc t                                    21

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: CDRL2

<400> SEQUENCE: 13

Ala Thr Ser Ala Leu Ala Ser
1               5

<210> SEQ ID NO 14
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(21)
<223> OTHER INFORMATION: CDRL2

<400> SEQUENCE: 14
gccacatccg ctctggcttc t                                    21

<210> SEQ ID NO 15
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(9)
<223> OTHER INFORMATION: CDRL3

<400> SEQUENCE: 15

Gln Gln Trp Thr Ser Asn Pro Pro Thr
1               5

<210> SEQ ID NO 16
```

```
<211> LENGTH: 27
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(27)
<223> OTHER INFORMATION: CDRL3

<400> SEQUENCE: 16
cagcagtgga ctagtaaccc acccacg                                           27

<210> SEQ ID NO 17
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(9)
<223> OTHER INFORMATION: CDRL3

<400> SEQUENCE: 17

Gln Gln Trp Thr Phe Asn Pro Pro Thr
1               5

<210> SEQ ID NO 18
<211> LENGTH: 27
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(27)
<223> OTHER INFORMATION: CDRL3

<400> SEQUENCE: 18
cagcagtgga cttttaaccc acccacg                                           27

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(9)
<223> OTHER INFORMATION: CDRL3

<400> SEQUENCE: 19

Gln Gln Trp Leu Ser Asn Pro Pro Thr
1               5

<210> SEQ ID NO 20
<211> LENGTH: 27
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(27)
<223> OTHER INFORMATION: CDRL3

<400> SEQUENCE: 20
cagcagtggc tgagtaaccc acccact                                           27
```

```
<210> SEQ ID NO 21
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(9)
<223> OTHER INFORMATION: CDRL3

<400> SEQUENCE: 21

Gln Thr Trp Thr Phe Asn Pro Pro Thr
1               5

<210> SEQ ID NO 22
<211> LENGTH: 27
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(27)
<223> OTHER INFORMATION: CDRL3

<400> SEQUENCE: 22
cagacttgga cttttaaccc tcccacg                                        27

<210> SEQ ID NO 23
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(10)
<223> OTHER INFORMATION: CDRH1

<400> SEQUENCE: 23

Gly Tyr Thr Phe Thr Ser Tyr Asn Met His
1               5                   10

<210> SEQ ID NO 24
<211> LENGTH: 30
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(30)
<223> OTHER INFORMATION: CDRH1

<400> SEQUENCE: 24
ggatacacct tcaccagcta caatatgcac                                     30

<210> SEQ ID NO 25
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(10)
<223> OTHER INFORMATION: CDRH1

<400> SEQUENCE: 25
```

```
Gly Arg Thr Phe Thr Ser Tyr Asn Met His
1               5                   10
```

<210> SEQ ID NO 26
<211> LENGTH: 30
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(30)
<223> OTHER INFORMATION: CDRH1

<400> SEQUENCE: 26

```
ggccgtacat ttaccagtta caatatgcac                                30
```

<210> SEQ ID NO 27
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(17)
<223> OTHER INFORMATION: CDRH2

<400> SEQUENCE: 27

```
Ala Ile Tyr Pro Gly Asn Gly Asp Thr Ser Tyr Asn Gln Lys Phe Lys
1               5                   10                  15
Gly
```

<210> SEQ ID NO 28
<211> LENGTH: 51
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(51)
<223> OTHER INFORMATION: CDRH2

<400> SEQUENCE: 28

```
gccatctatc ctggaaatgg tgatacaagc tacaatcaga gttcaaaggc           51
```

<210> SEQ ID NO 29
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(17)
<223> OTHER INFORMATION: CDRH2

<400> SEQUENCE: 29

```
Ala Ile Tyr Pro Gly Asn Gly Asp Thr Ser Tyr Asn His Lys His Lys
1               5                   10                  15
Gly
```

<210> SEQ ID NO 30
<211> LENGTH: 51
<212> TYPE: DNA
<213> ORGANISM: Artificial Sequence
<220> FEATURE:
<223> OTHER INFORMATION: Synthetic Construct

```
<220> FEATURE:
<221> NAME/KEY: misc_feature
<222> LOCATION: (1)..(51)
<223> OTHER INFORMATION: CDRH2

<400> SEQUENCE: 30
gccatctatc ctggaaatgg tgatacaagc tacaatcata agcataaagg g            51

<210> SEQ ID NO 31
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(17)
<223> OTHER INFORMATION: CDRH2

<400> SEQUENCE: 31

Ala Ile Tyr Pro Gly Asn Gly Asp Thr Ser Tyr Asn Gln Lys Phe Lys
1               5                   10                  15

Trp

<210> SEQ ID NO 32
<211> LENGTH: 51
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(51)
<223> OTHER INFORMATION: CDRH2

<400> SEQUENCE: 32
gccatctatc ctggaaatgg tgatacaagc tacaatcaga agtttaaatg g            51

<210> SEQ ID NO 33
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(17)
<223> OTHER INFORMATION: CDRH2

<400> SEQUENCE: 33

Ala Ile Tyr Pro Leu Asn Gly Asp Thr Ser Tyr Asn Gln Lys Phe Lys
1               5                   10                  15

Leu

<210> SEQ ID NO 34
<211> LENGTH: 51
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(51)
<223> OTHER INFORMATION: CDRH2

<400> SEQUENCE: 34
gctatttatc ccttgaatgg tgatacttcc tacaatcaga agttcaaact c            51
```

```
<210> SEQ ID NO 35
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(17)
<223> OTHER INFORMATION: CDRH2

<400> SEQUENCE: 35

Ala Ile Tyr Pro Leu Asn Gly Asp Thr Ser Tyr Asn Arg Lys Ser Lys
1               5                   10                  15

Leu

<210> SEQ ID NO 36
<211> LENGTH: 52
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(52)
<223> OTHER INFORMATION: CDRH2

<400> SEQUENCE: 36
gctattttat cccttgaatg gtgatacttc ctacaatcgt aagtcgaaac tc            52

<210> SEQ ID NO 37
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(17)
<223> OTHER INFORMATION: CDRH2

<400> SEQUENCE: 37

Ala Ile Tyr Pro Leu Thr Gly Asp Thr Ser Tyr Asn Gln Lys Phe Lys
1               5                   10                  15

Leu

<210> SEQ ID NO 38
<211> LENGTH: 51
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(51)
<223> OTHER INFORMATION: CDRH2

<400> SEQUENCE: 38
gctatttatc ccttgacggg tgatacttcc tacaatcaga agttcaaact c             51

<210> SEQ ID NO 39
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(17)
<223> OTHER INFORMATION: CDRH2
```

```
<400> SEQUENCE: 39

Ala Ile Tyr Pro Leu Thr Gly Asp Thr Ser Tyr Asn Gln Lys Ser Lys
1               5                   10                  15

Leu

<210> SEQ ID NO 40
<211> LENGTH: 51
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(51)
<223> OTHER INFORMATION: CDRH2

<400> SEQUENCE: 40
gctatttatc ccttgacggg tgatacttcc tacaatcaga agtcgaaact c            51

<210> SEQ ID NO 41
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(12)
<223> OTHER INFORMATION: CDRH3

<400> SEQUENCE: 41

Ser Thr Tyr Tyr Gly Gly Asp Trp Tyr Phe Asp Val
1               5                   10

<210> SEQ ID NO 42
<211> LENGTH: 36
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(36)
<223> OTHER INFORMATION: CDRH3

<400> SEQUENCE: 42
tcgacttact acggcggtga ctggtacttc gatgtc                             36

<210> SEQ ID NO 43
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(12)
<223> OTHER INFORMATION: CDRH3

<400> SEQUENCE: 43

Ser Thr Tyr Tyr Gly Gly Asp Trp Gln Phe Asp Val
1               5                   10

<210> SEQ ID NO 44
<211> LENGTH: 36
<212> TYPE: DNA
<213> ORGANISM: Artificial Sequence
<220> FEATURE:
```

```
<223> OTHER INFORMATION: Synthetic Construct
<220> FEATURE:
<221> NAME/KEY: misc_feature
<222> LOCATION: (1)..(36)
<223> OTHER INFORMATION: CDRH3

<400> SEQUENCE: 44
tcgacttact acggcggtga ctggcagttc gacgtc                                     36

<210> SEQ ID NO 45
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(12)
<223> OTHER INFORMATION: CDRH3

<400> SEQUENCE: 45

Ser Thr Tyr Tyr Gly Gly Asp Trp Gln Phe Asp Glu
1               5                   10

<210> SEQ ID NO 46
<211> LENGTH: 36
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(36)
<223> OTHER INFORMATION: CDRH3

<400> SEQUENCE: 46
tcgacttatt acggcggtga ctggcagttc gacgag                                     36

<210> SEQ ID NO 47
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(12)
<223> OTHER INFORMATION: CDRH3

<400> SEQUENCE: 47

Ser Thr Tyr Tyr Gly Gly Asp Trp Gln Phe Asp Gln
1               5                   10

<210> SEQ ID NO 48
<211> LENGTH: 36
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(36)
<223> OTHER INFORMATION: CDRH3

<400> SEQUENCE: 48
tcgacttatt acggcggtga ctggcagttc gaccag                                     36

<210> SEQ ID NO 49
<211> LENGTH: 12
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(12)
<223> OTHER INFORMATION: CDRH3

<400> SEQUENCE: 49

Ser Thr Tyr Tyr Gly Gly Asp Trp Ser Phe Asp Val
1               5                   10

<210> SEQ ID NO 50
<211> LENGTH: 36
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(36)
<223> OTHER INFORMATION: CDRH3

<400> SEQUENCE: 50
tcgacttact acggcggtga ctggagtttc gatgtc                              36

<210> SEQ ID NO 51
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(12)
<223> OTHER INFORMATION: CDRH3

<400> SEQUENCE: 51

Ser Thr Tyr Tyr Gly Gly Asp Trp Thr Phe Asp Val
1               5                   10

<210> SEQ ID NO 52
<211> LENGTH: 36
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(36)
<223> OTHER INFORMATION: CDRH3

<400> SEQUENCE: 52
tcgacttact acggcggtga ctggactttc gatgtc                              36

<210> SEQ ID NO 53
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(12)
<223> OTHER INFORMATION: CDRH3

<400> SEQUENCE: 53

Ser Thr Tyr Val Gly Gly Asp Trp Thr Phe Asp Val
1               5                   10
```

```
<210> SEQ ID NO 54
<211> LENGTH: 36
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(36)
<223> OTHER INFORMATION: CDRH3

<400> SEQUENCE: 54
tcgacttacg tgggcggtga ctggactttc gatgtc                           36

<210> SEQ ID NO 55
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(12)
<223> OTHER INFORMATION: CDRH3

<400> SEQUENCE: 55

Ser Tyr Tyr Val Gly Gly Asp Trp Thr Phe Asp Val
1               5                   10

<210> SEQ ID NO 56
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(34)
<223> OTHER INFORMATION: CDRH3

<400> SEQUENCE: 56
tcgtattacg tgggcggtga ctggacmcga tgtc                             34

<210> SEQ ID NO 57
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(12)
<223> OTHER INFORMATION: CDRH3

<400> SEQUENCE: 57

Ser Thr Tyr Val Gly Gly Asp Trp Gln Phe Asp Val
1               5                   10

<210> SEQ ID NO 58
<211> LENGTH: 36
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(36)
<223> OTHER INFORMATION: CDRH3

<400> SEQUENCE: 58
tcgacttacg tgggcggtga ctggcagttc gatgtc                           36
```

<210> SEQ ID NO 59
<211> LENGTH: 106
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(106)
<223> OTHER INFORMATION: CDRL1

<400> SEQUENCE: 59

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Pro Tyr Ile
            20                  25                  30

His Trp Tyr Gln Gln Lys Pro Gly Gln Ala Pro Arg Leu Leu Ile Tyr
        35                  40                  45

Ala Thr Ser Ala Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Leu Ser Asn Pro Pro Thr
                85                  90                  95

Phe Gly Gln Gly Thr Lys Leu Glu Ile Lys
            100                 105
```

<210> SEQ ID NO 60
<211> LENGTH: 318
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(318)
<223> OTHER INFORMATION: CDRL1

<400> SEQUENCE: 60

```
gaaattgtgt tgacgcagtc tccaggcacc ctgtctttgt ctccagggga aagagccacc      60
ctctcctgca gggccagctc aagtgtaccg tacatccact ggtaccagca gaaacctggc     120
caggctccca ggctcctcat ctatgccaca tccgctctgg cttctggcat cccagacagg     180
ttcagtggca gtgggtctgg gacagacttc actctcacca tcagcagact ggagcctgaa     240
gattttgcag tgtattactg tcagcagtgg ctgagtaacc cacccacttt tggccagggg     300
accaagctgg agatcaaa                                                   318
```

<210> SEQ ID NO 61
<211> LENGTH: 121
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(121)
<223> OTHER INFORMATION: CDRH1

<400> SEQUENCE: 61

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Arg Thr Phe Thr Ser Tyr
```

```
                    20                  25                  30
Asn Met His Trp Val Arg Gln Met Pro Gly Lys Gly Leu Glu Trp Met
        35                  40                  45

Gly Ala Ile Tyr Pro Leu Thr Gly Asp Thr Ser Tyr Asn Gln Lys Ser
    50                  55                  60

Lys Leu Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Thr Tyr Val Gly Gly Asp Trp Gln Phe Asp Val Trp Gly
            100                 105                 110

Lys Gly Thr Thr Val Thr Val Ser Ser
            115                 120

<210> SEQ ID NO 62
<211> LENGTH: 363
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(363)
<223> OTHER INFORMATION: CDRH1

<400> SEQUENCE: 62
gaggtgcagc tggtgcagtc tggagcagag gtgaaaaagc ccggggagtc tctgaagatc      60
tcctgtaagg gttctggccg tacatttacc agttacaata tgcactgggt gcgccagatg     120
cccgggaaag gcctggagtg gatgggggct atttatccct tgacgggtga tacttcctac     180
aatcagaagt cgaaactcca ggtcaccatc tcagccgaca gtccatcag caccgcctac      240 ctgcagtgga gcagcctgaa ggcctcggac accgccatgt attactgtgc gagatcgact     300
tacgtgggcg gtgactggca gttcgatgtc tggggcaagg ggaccacggt caccgtctcc     360
tca                                                                  363

<210> SEQ ID NO 63
<211> LENGTH: 106
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(106)
<223> OTHER INFORMATION: CDRL1

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val His Tyr Ile
            20                  25                  30

His Trp Tyr Gln Gln Lys Pro Gly Lys Val Pro Lys Leu Leu Ile Tyr
        35                  40                  45

Ala Thr Ser Gly Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Val Ala Thr Tyr Tyr Cys Gln Thr Trp Thr Phe Asn Pro Pro Thr
                85                  90                  95
```

Phe Gly Gly Gly Thr Lys Val Glu Ile Lys
            100                 105

<210> SEQ ID NO 64
<211> LENGTH: 318
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(318)
<223> OTHER INFORMATION: CDRL1

<400> SEQUENCE: 64
gacatccaga tgacccagtc tccatcctcc ctgtctgcat ctgtaggaga cagagtcacc    60
atcacttgca gggccagctc aagtgtacat tacatccact ggtaccagca gaaaccaggg   120
aaagttccta agctcttgat ctatgccaca tccggcctgg cttctggggt cccatctcgg   180
ttcagtggca gtggatctgg gacagatttc actctcacca tcagcagcct gcagcctgaa   240
gatgttgcca cttattactg ccagacttgg acttttaacc ctcccacgtt cggcggaggg   300
accaaggtgg agatcaaa                                                 318

<210> SEQ ID NO 65
<211> LENGTH: 121
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(121)
<223> OTHER INFORMATION: CDRH1

<400> SEQUENCE: 65

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Ala Ile Tyr Pro Gly Asn Gly Asp Thr Ser Tyr Asn Gln Lys Phe
    50                  55                  60

Lys Trp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Gly Gly Asp Trp Gln Phe Asp Glu Trp Gly
            100                 105                 110

Lys Gly Thr Thr Val Thr Val Ser Ser
        115                 120

<210> SEQ ID NO 66
<211> LENGTH: 363
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(363)
<223> OTHER INFORMATION: CDRH1

<400> SEQUENCE: 66

```
caggtgcagc tggtgcagtc tggtgctgaa gtgaagaagc ctggggcctc agtgaaggtg      60
tcctgcaagg catctggata caccttcacc agctacaata tgcactgggt gcgacaggcc     120
cctggacaag gcttgagtg gatgggagcc atctatcctg gaaatggtga tacaagctac     180
aatcagaagt ttaaatggag agtcaccatg accagggaca cgtccacgag cacagtctac     240
atggagctga gcagcctgag atctgaggac acggccgtgt attactgtgc gagatcgact     300
tattacggcg gtgactggca gttcgacgag tggggcaaag gaccacggt caccgtctcc     360 tca                                                                   363
```

<210> SEQ ID NO 67  
<211> LENGTH: 213  
<212> TYPE: PRT  
<213> ORGANISM: Artificial Sequence  
<220> FEATURE:  
<223> OTHER INFORMATION: Synthetic Construct  
<220> FEATURE:  
<221> NAME/KEY: MISC_FEATURE  
<222> LOCATION: (1)..(213)  
<223> OTHER INFORMATION: CDRL1

<400> SEQUENCE: 67

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Pro Tyr Ile
            20                  25                  30

His Trp Tyr Gln Gln Lys Pro Gly Gln Ala Pro Arg Leu Leu Ile Tyr
        35                  40                  45

Ala Thr Ser Ala Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Leu Ser Asn Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 68  
<211> LENGTH: 642  
<212> TYPE: DNA  
<213> ORGANISM: Artificial Sequence  
<220> FEATURE:  
<223> OTHER INFORMATION: Synthetic Construct  
<220> FEATURE:  
<221> NAME/KEY: misc_feature

<222> LOCATION: (1)..(642)
<223> OTHER INFORMATION: CDRL1

<400> SEQUENCE: 68

```
gaaattgtgt tgacgcagtc tccaggcacc ctgtctttgt ctccagggga aagagccacc      60
ctctcctgca gggccagctc aagtgtaccg tacatccact ggtaccagca gaaacctggc     120
caggctccca ggctcctcat ctatgccaca tccgctctgg cttctggcat cccagacagg     180
ttcagtggca gtgggtctgg gacagacttc actctcacca tcagcagact ggagcctgaa     240
gattttgcag tgtattactg tcagcagtgg ctgagtaacc cacccacttt tggccagggg     300
accaagctgg agatcaaacg aactgtggct gcaccatctg tcttcatctt cccgccatct     360
gatgagcagt tgaaatctgg aactgcctct gttgtgtgcc tgctgaataa cttctatccc     420
agagaggcca aagtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgtt ag                        642
```

<210> SEQ ID NO 69
<211> LENGTH: 451
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(451)
<223> OTHER INFORMATION: CDRH1

<400> SEQUENCE: 69

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Arg Thr Phe Thr Ser Tyr
            20                  25                  30

Asn Met His Trp Val Arg Gln Met Pro Gly Lys Gly Leu Glu Trp Met
        35                  40                  45

Gly Ala Ile Tyr Pro Leu Thr Gly Asp Thr Ser Tyr Asn Gln Lys Ser
    50                  55                  60

Lys Leu Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Thr Tyr Val Gly Gly Asp Trp Gln Phe Asp Val Trp Gly
            100                 105                 110

Lys Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

```
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Asp Glu Leu Thr Lys Asn Gln Val Ser
            355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
Pro Gly Lys
    450

<210> SEQ ID NO 70
<211> LENGTH: 1356
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1356)
<223> OTHER INFORMATION: CDRH1

<400> SEQUENCE: 70
gaggtgcagc tggtgcagtc tggagcagag gtgaaaaagc ccggggagtc tctgaagatc      60
tcctgtaagg gttctggccg tacatttacc agttacaata tgcactgggt gcgccagatg     120
cccgggaaag gcctggagtg gatggggggct atttatccct tgacgggtga tacttcctac     180
aatcagaagt cgaaactcca ggtcaccatc tcagccgaca gtccatcagc accgcctac      240
ctgcagtgga gcagcctgaa ggcctcggac accgccatgt attactgtgc gagatcgact     300
tacgtgggcg tgactggca gttcgatgtc tggggcaagg gaccacggt caccgtctcc       360
tcagcctcca ccaagggccc atcggtcttc cccctggcac cctcctccaa gagcacctct     420
gggggcacag cggccctggg ctgcctggtc aaggactact ccccgaacc ggtgacggtg      480
tcgtggaact caggcgccct gaccagcggc gtgcacacct tcccggctgt cctacagtcc     540
```

```
tcaggactct actccctcag cagcgtggtg accgtgccct ccagcagctt gggcacccag    600
acctacatct gcaacgtgaa tcacaagccc agcaacacca aggtggacaa gaaggttgag    660
cccaaatctt gtgacaaaac tcacacatgc ccaccgtgcc cagcacctga actcctgggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga aaaaccatc    1020 tccaaagcca aagggcagcc ccgagaacca caggtgtaca ccctgccccc atcccgggac   1080
gagctgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tatagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaatga                            1356
```

<210> SEQ ID NO 71
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(23)
<223> OTHER INFORMATION: FRL1

<400> SEQUENCE: 71

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 72
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(15)
<223> OTHER INFORMATION: FRL2

<400> SEQUENCE: 72

Trp Tyr Gln Gln Lys Pro Gly Gln Ala Pro Arg Leu Leu Ile Tyr
1               5                   10                  15

<210> SEQ ID NO 73
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(32)
<223> OTHER INFORMATION: FRL3

<400> SEQUENCE: 73

Gly Ile Pro Asp Arg Phe Ser Gly Ser Gly Ser Gly Thr Asp Phe Thr

```
                 1               5                  10                 15
Leu Thr Ile Ser Arg Leu Glu Pro Glu Asp Phe Ala Val Tyr Tyr Cys
                    20                  25                  30

<210> SEQ ID NO 74
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(10)
<223> OTHER INFORMATION: FRL4

<400> SEQUENCE: 74

Phe Gly Gln Gly Thr Lys Leu Glu Ile Lys
1               5                  10

<210> SEQ ID NO 75
<211> LENGTH: 69
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(69)
<223> OTHER INFORMATION: FRL1

<400> SEQUENCE: 75
gaaattgtgt tgacgcagtc tccaggcacc ctgtctttgt ctccagggga aagagccacc    60
ctctcctgc                                                           69

<210> SEQ ID NO 76
<211> LENGTH: 45
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(45)
<223> OTHER INFORMATION: FRL2

<400> SEQUENCE: 76
tggtaccagc agaaacctgg ccaggctccc aggctcctca tctat                   45

<210> SEQ ID NO 77
<211> LENGTH: 96
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(96)
<223> OTHER INFORMATION: FRL3

<400> SEQUENCE: 77
ggcatcccag acaggttcag tggcagtggg tctgggacag acttcactct caccatcagc    60
agactggagc ctgaagattt tgcagtgtat tactgt                             96

<210> SEQ ID NO 78
<211> LENGTH: 30
<212> TYPE: DNA
<213> ORGANISM: Artificial Sequence
<220> FEATURE:
```

-continued

<223> OTHER INFORMATION: Synthetic Construct
<220> FEATURE:
<221> NAME/KEY: misc_feature
<222> LOCATION: (1)..(30)
<223> OTHER INFORMATION: FRL4

<400> SEQUENCE: 78
tttggccagg ggaccaagct ggagatcaaa                                      30

<210> SEQ ID NO 79
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(25)
<223> OTHER INFORMATION: FRH1

<400> SEQUENCE: 79

Glu Val Gln Leu Val Gln Ser Gly Ala Glu Val Lys Lys Pro Gly Glu
1               5                   10                  15

Ser Leu Lys Ile Ser Cys Lys Gly Ser
            20                  25

<210> SEQ ID NO 80
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(14)
<223> OTHER INFORMATION: FRH2

<400> SEQUENCE: 80

Trp Val Arg Gln Met Pro Gly Lys Gly Leu Glu Trp Met Gly
1               5                   10

<210> SEQ ID NO 81
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(32)
<223> OTHER INFORMATION: FRH3

<400> SEQUENCE: 81

Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30

<210> SEQ ID NO 82
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(11)
<223> OTHER INFORMATION: FRH4

<400> SEQUENCE: 82

```
Trp Gly Lys Gly Thr Thr Val Thr Val Ser Ser
1               5                   10
```

<210> SEQ ID NO 83
<211> LENGTH: 75
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(75)
<223> OTHER INFORMATION: FRH1

<400> SEQUENCE: 83
gaggtgcagc tggtgcagtc tggagcagag gtgaaaaagc ccggggagtc tctgaagatc    60
tcctgtaagg gttct                                                     75

<210> SEQ ID NO 84
<211> LENGTH: 42
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(42)
<223> OTHER INFORMATION: FRH2

<400> SEQUENCE: 84
tgggtgcgcc agatgcccgg gaaaggcctg gagtggatgg gg                       42

<210> SEQ ID NO 85
<211> LENGTH: 96
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(96)
<223> OTHER INFORMATION: FRH3

<400> SEQUENCE: 85
caggtcacca tctcagccga caagtccatc agcaccgcct acctgcagtg gagcagcctg    60
aaggcctcgg acaccgccat gtattactgt gcgaga                              96

<210> SEQ ID NO 86
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(33)
<223> OTHER INFORMATION: FRH4

<400> SEQUENCE: 86
tggggcaagg ggaccacggt caccgtctcc tca                                 33

<210> SEQ ID NO 87
<211> LENGTH: 23
<212> TYPE: PRT
<213> ORGANISM: Artificial Sequence
<220> FEATURE:
<223> OTHER INFORMATION: Synthetic Construct
<220> FEATURE:

```
<221> NAME/KEY: MISC_FEATURE
<222> LOCATION: (1)..(23)
<223> OTHER INFORMATION: FRL1

<400> SEQUENCE: 87

Asp Ile Gln Met Thr Gln Ser Pro Ser Ser Leu Ser Ala Ser Val Gly
1               5                   10                  15
Asp Arg Val Thr Ile Thr Cys
            20

<210> SEQ ID NO 88
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(15)
<223> OTHER INFORMATION: FRL2

<400> SEQUENCE: 88

Trp Tyr Gln Gln Lys Pro Gly Lys Val Pro Lys Leu Leu Ile Tyr
1               5                   10                  15

<210> SEQ ID NO 89
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(32)
<223> OTHER INFORMATION: FRL3

<400> SEQUENCE: 89

Gly Val Pro Ser Arg Phe Ser Gly Ser Gly Ser Gly Thr Asp Phe Thr
1               5                   10                  15
Leu Thr Ile Ser Ser Leu Gln Pro Glu Asp Val Ala Thr Tyr Tyr Cys
            20                  25                  30

<210> SEQ ID NO 90
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(10)
<223> OTHER INFORMATION: FRL4

<400> SEQUENCE: 90

Phe Gly Gly Gly Thr Lys Val Glu Ile Lys
1               5                   10

<210> SEQ ID NO 91
<211> LENGTH: 69
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(69)
<223> OTHER INFORMATION: FRL1

<400> SEQUENCE: 91
```

```
gacatccaga tgacccagtc tccatcctcc ctgtctgcat ctgtaggaga cagagtcacc    60
atcacttgc                                                            69
```

<210> SEQ ID NO 92
<211> LENGTH: 45
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(45)
<223> OTHER INFORMATION: FRL2

<400> SEQUENCE: 92

```
tggtaccagc agaaaccagg gaaagttcct aagctcttga tctat                    45
```

<210> SEQ ID NO 93
<211> LENGTH: 96
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(96)
<223> OTHER INFORMATION: FRL3

<400> SEQUENCE: 93

```
ggggtcccat ctcggttcag tggcagtgga tctgggacag atttcactct caccatcagc    60
agcctgcagc ctgaagatgt tgccacttat tactgc                              96
```

<210> SEQ ID NO 94
<211> LENGTH: 30
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(30)
<223> OTHER INFORMATION: FRL4

<400> SEQUENCE: 94

```
ttcggcggag ggaccaaggt ggagatcaaa                                     30
```

<210> SEQ ID NO 95
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(25)
<223> OTHER INFORMATION: FRH1

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 96
<211> LENGTH: 14
<212> TYPE: PRT
<213> ORGANISM: Artificial Sequence
<220> FEATURE:

-continued

<223> OTHER INFORMATION: Synthetic Construct
<220> FEATURE:
<221> NAME/KEY: MISC_FEATURE
<222> LOCATION: (1)..(14)
<223> OTHER INFORMATION: FRH2

<400> SEQUENCE: 96

Trp Val Arg Gln Ala Pro Gly Gln Gly Leu Glu Trp Met Gly
1               5                   10

<210> SEQ ID NO 97
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(32)
<223> OTHER INFORMATION: FRH3

<400> SEQUENCE: 97

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 98
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(11)
<223> OTHER INFORMATION: FRH4

<400> SEQUENCE: 98

Trp Gly Lys Gly Thr Thr Val Thr Val Ser Ser
1               5                   10

<210> SEQ ID NO 99
<211> LENGTH: 75
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(75)
<223> OTHER INFORMATION: FRH1

<400> SEQUENCE: 99
caggtgcagc tggtgcagtc tggtgctgaa gtgaagaagc ctggggcctc agtgaaggtg     60
tcctgcaagg catct                                                      75

<210> SEQ ID NO 100
<211> LENGTH: 42
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(42)
<223> OTHER INFORMATION: FRH2

<400> SEQUENCE: 100

-continued

```
tgggtgcgac aggcccctgg acaagggctt gagtggatgg ga                42

<210> SEQ ID NO 101
<211> LENGTH: 96
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(96)
<223> OTHER INFORMATION: FRH3

<400> SEQUENCE: 101
agagtcacca tgaccaggga cacgtccacg agcacagtct acatggagct gagcagcctg    60
agatctgagg acacggccgt gtattactgt gcgaga                             96

<210> SEQ ID NO 102
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(33)
<223> OTHER INFORMATION: FRH4

<400> SEQUENCE: 102
tggggcaaag ggaccacggt caccgtctcc tca                                33
```